United States Patent
Hanagata et al.

(10) Patent No.: US 9,492,826 B2
(45) Date of Patent: Nov. 15, 2016

(54) MICROFLUIDIC DEVICES WITH INTEGRATED RESISTIVE HEATER ELECTRODES INCLUDING SYSTEMS AND METHODS FOR CONTROLLING AND MEASURING THE TEMPERATURES OF SUCH HEATER ELECTRODES

(75) Inventors: Takayoshi Hanagata, Rockville, MD (US); Hiroshi Inoue, Bethesda, MD (US); Gregory A. Dale, Gaithersburg, MD (US); Kenton C. Hasson, Gaithersburg, MD (US)

(73) Assignee: Canon U.S. Life Sciences, Inc., Rockville, MD (US)

( * ) Notice: Subject to any disclaimer, the term of this patent is extended or adjusted under 35 U.S.C. 154(b) by 968 days.

(21) Appl. No.: 12/165,013

(22) Filed: Jun. 30, 2008

(65) Prior Publication Data
US 2009/0061489 A1 Mar. 5, 2009

Related U.S. Application Data

(60) Provisional application No. 60/968,760, filed on Aug. 29, 2007.

(51) Int. Cl.
*B01L 7/00* (2006.01)
*G01N 25/00* (2006.01)
*B01L 3/00* (2006.01)

(52) U.S. Cl.
CPC ............ *B01L 7/52* (2013.01); *B01L 3/502715* (2013.01); *B01L 7/525* (2013.01); *B01L 3/5027* (2013.01); *B01L 2300/0816* (2013.01); *B01L 2300/1827* (2013.01); *B01L 2300/1833* (2013.01)

(58) Field of Classification Search
CPC ................. B01L 7/527; B01L 3/5027; B01L 2300/0816; B01L 2300/1827

USPC ....... 219/182, 483, 484, 485, 486, 490, 494, 219/497, 499, 506; 422/81, 503, 68.1; 435/91.2, 6
See application file for complete search history.

(56) References Cited

U.S. PATENT DOCUMENTS 4,723,129 A   2/1988   Endo et al.
5,965,410 A   10/1999  Chow et al.
(Continued)

FOREIGN PATENT DOCUMENTS

WO    96/41864 A1      12/1996
WO    2005/075683 A1   8/2005

OTHER PUBLICATIONS

Woodley et al., Functional integration of PCR amplification and capillary electrophoresis in a microfabricated DNA analysis device, Analytical Chemistry, 1996, vol. 68, No. 23, 4081-5086.*
(Continued)

*Primary Examiner* — Lyle Alexander
*Assistant Examiner* — Robert Eom
(74) *Attorney, Agent, or Firm* — Rothwell, Figg, Ernst & Manbeck, P.C.

(57) ABSTRACT

The invention relates to methods and devices for control of an integrated thin-film device with a plurality of microfluidic channels. In one embodiment, the microfluidic device includes a microfluidic chip comprising a first zone having a plurality of microfluidic channels and a second zone having a plurality of microfluidic channels, wherein the microfluidic channels in the first and second zones are in fluid communication. The microfluidic device further comprising a thin-film heater in thermal communication with each of the microfluidic channels in the first and second zones. The microfluidic device also includes a control system configured to independently control the temperature of each of the thin-film heaters using pulse width modulation (PWM) control signals that are optimized for each of the thin-film heaters.

18 Claims, 25 Drawing Sheets

(56) References Cited

U.S. PATENT DOCUMENTS

| | | | |
|---|---|---|---|
| 5,985,651 | A | 11/1999 | Hunicke-Smith |
| 6,022,095 | A | 2/2000 | Narang et al. |
| 6,068,751 | A | 5/2000 | Neukermans |
| 6,116,710 | A | 9/2000 | Tajika et al. |
| 6,132,996 | A | 10/2000 | Hunicke-Smith |
| 6,174,675 | B1 | 1/2001 | Chow et al. |
| 6,252,209 | B1 * | 6/2001 | Liepold .................. 219/501 |
| 6,310,636 | B1 | 10/2001 | Tajika et al. |
| 6,326,211 | B1 | 12/2001 | Anderson et al. |
| 6,375,312 | B1 | 4/2002 | Ikeda et al. |
| 6,413,766 | B2 | 7/2002 | Landers et al. |
| 6,537,799 | B2 | 3/2003 | Chow et al. |
| 6,568,779 | B1 | 5/2003 | Pulman et al. |
| 6,664,104 | B2 | 12/2003 | Pourahmadi et al. |
| 6,905,195 | B2 | 6/2005 | Silverbrook |
| 6,929,730 | B2 | 8/2005 | Lee et al. |
| 6,945,633 | B2 | 9/2005 | Imanaka et al. |
| 6,960,437 | B2 | 11/2005 | Enzelberger et al. |
| 7,041,481 | B2 | 5/2006 | Anderson et al. |
| 7,060,948 | B2 | 6/2006 | Cho et al. |
| 7,080,895 | B2 | 7/2006 | Silverbrook |
| 7,156,499 | B2 | 1/2007 | Suzuki et al. |
| 7,165,823 | B2 | 1/2007 | Yakura et al. |
| 7,168,167 | B2 | 1/2007 | Silverbrook |
| 7,195,036 | B2 | 3/2007 | Burns et al. |
| 7,338,637 | B2 | 3/2008 | Pease et al. |
| 2002/0072112 | A1 | 6/2002 | Atwood et al. |
| 2002/0143437 | A1 * | 10/2002 | Handique et al. ............ 422/100 |
| 2002/0191826 | A1 | 12/2002 | Benett et al. |
| 2003/0138941 | A1 | 7/2003 | Gong et al. |
| 2003/0155344 | A1 | 8/2003 | Cobb |
| 2004/0086927 | A1 | 5/2004 | Atwood et al. |
| 2004/0219732 | A1 | 11/2004 | Burns et al. |
| 2005/0042639 | A1 | 2/2005 | Knapp et al. |
| 2005/0084424 | A1 | 4/2005 | Ganesan et al. |
| 2005/0134621 | A1 | 6/2005 | Miyakoshi et al. |
| 2005/0191708 | A1 | 9/2005 | Saul et al. |
| 2006/0188979 | A1 | 8/2006 | Spaid et al. |
| 2007/0128381 | A1 | 6/2007 | Yajima |
| 2007/0159512 | A1 | 7/2007 | Shirota et al. |
| 2008/0032347 | A1 | 2/2008 | Sarofim et al. |

OTHER PUBLICATIONS

Luo, Ching-Hsing, et al. "A Portable Polymerase Chain Reaction Device by MEMS and Neural Network Technologies." Asia-Pacific Conference of Transducerss and Micro-Nano Technology, Sapporo, Japan. 2004.*

Cho et al., "PDMS-glass serpentine microchannel chip for time domain PCR with bubble suppression in sample injection," J. Micromech. Microeng., vol. 17, (2007) pp. 1810-1817.

El-Ali et al., "Simulation and experimental validation of a SU-8 based PCR thermocycler chip with integrated heaters and temperature sensor," Sensors and Actuators, A 110 (2004) pp. 3-10.

Imran et al., "Thermal response of an on-chip assembly of RTD heaters, sputtered sample and microthermocouples," Sensors and Actuators, A 121 (2005) pp. 306-320.

Lagally et al., "Fully integrated PCR-capillary electrophoresis microsystem for DNA analysis," Lab on a Chip, vol. 1 (2001) pp. 102-107.

Lee et al., "A miniaturized DNA amplifier: Its application in traditional Chinese medicine," Anal. Chem., vol. 72 (2000) pp. 4242-4247.

Liu et al., "Multichannel PCR-CE microdevice for genetic analysis," Anal. Chem., vol. 78 (2006) pp. 5474-5479.

Zhang et al., "Fabrication, modeling and testing of a thin film Au/Ti microheater," International Journal of Thermal Sciences, vol. 46 (2007) pp. 580-588.

Lagally et al., "Single-Molecule DNA Amplification and Analysis in an Integrated Microfluidic Device," Analytical Chemistry, vol. 73, No. 3, (2001) pp. 565-570.

Kopp et al., "Chemical Amplification: Continuous-Flow PCR on a Chip," Science, vol. 280, (1998) pp. 1046-1048.

Park et al., "Cylindrical compact thermal-cycling device for continuous-flow polymerase chain reaction," Analytical Chemistry, vol. 75 (2003) pp. 6029-6033.

Pal, et al., "An integrated microfluidic device for influenza and other genetic analyses," RSC Lab on a Chip, vol. 5, (2005) pp. 1024-1032.

* cited by examiner

MICROFLUIDIC DEVICES WITH INTEGRATED RESISTIVE HEATER ELECTRODES INCLUDING SYSTEMS AND METHODS FOR CONTROLLING AND MEASURING THE TEMPERATURES OF SUCH HEATER ELECTRODES

CROSS REFERENCE TO RELATED APPLICATION

This application claims the benefit of Provisional Patent Application Ser. No. 60/968,760, filed Aug. 29, 2007, which is incorporated herein by reference in its entirety.

BACKGROUND

1. Field of Invention

The present invention relates to microfluidic devices and temperature control of the microfluidic devices for performing biological reactions. More specifically, the present invention relates to systems and methods for determining and controlling the temperature of integrated thin film resistive heater elements in the microfluidic device.

2. Discussion of the Background

The detection of nucleic acids is central to medicine, forensic science, industrial processing, crop and animal breeding, and many other fields. The ability to detect disease conditions (e.g., cancer), infectious organisms (e.g., HIV), genetic lineage, genetic markers, and the like, is ubiquitous technology for disease diagnosis and prognosis, marker assisted selection, identification of crime scene features, the ability to propagate industrial organisms and many other techniques. Determination of the integrity of a nucleic acid of interest can be relevant to the pathology of an infection or cancer.

One of the most powerful and basic technologies to detect small quantities of nucleic acids is to replicate some or all of a nucleic acid sequence many times, and then analyze the amplification products. Polymerase chain reaction (PCR) is a well-known technique for amplifying DNA. With PCR, one can produce millions of copies of DNA starting from a single template DNA molecule. PCR includes phases of "denaturation," "annealing," and "extension." These phases are part of a cycle which is repeated a number of times so that at the end of the process there are enough copies to be detected and analyzed. For general details concerning PCR, see Sambrook and Russell, *Molecular Cloning—A Laboratory Manual* (3rd Ed.), Vols. 1-3, Cold Spring Harbor Laboratory, Cold Spring Harbor, N.Y. (2000); *Current Protocols in Molecular Biology*, F. M. Ausubel et al., eds., Current Protocols, a joint venture between Greene Publishing Associates, Inc. and John Wiley & Sons, Inc., (supplemented through 2005) and *PCR Protocols A Guide to Methods and Applications*, M. A. Innis et al., eds., Academic Press Inc. San Diego, Calif. (1990).

The PCR process phases of denaturing, annealing, and extension occur at different temperatures and cause target DNA molecule samples to replicate themselves. Temperature cycling (thermocyling) requirements vary with particular nucleic acid samples and assays. In the denaturing phase, a double stranded DNA (dsDNA) is thermally separated into single stranded DNA (ssDNA). During the annealing phase, primers are attached to the single stand DNA molecules. Single strand DNA molecules grow to double stranded DNA again in the extension phase through specific bindings between nucleotides in the PCR solution and the single strand DNA. Typical temperatures are 95° C. for denaturing, 55° C. for annealing, and 72° C. for extension. The temperature is held at each phase for a certain amount of time which may be a fraction of a second up to a few tens of seconds. The DNA is doubled at each cycle; it generally takes 20 to 40 cycles to produce enough DNA for the applications. To have good yield of target product, one has to accurately control the sample temperatures at the different phases to a specified degree.

More recently, a number of high throughput approaches to performing PCR and other amplification reactions have been developed, e.g., involving amplification reactions in microfluidic devices, as well as methods for detecting and analyzing amplified nucleic acids in or on the devices. Thermal cycling of the sample for amplification is usually accomplished in one of two methods. In the first method, the sample solution is loaded into the device and the temperature is cycled in time, much like a conventional PCR instrument. In the second method, the sample solution is pumped continuously through spatially varying temperature zones. See, for example, Lagally et al. (*Analytical Chemistry* 73:565-570 (2001)), Kopp et al. (*Science* 280:1046-1048 (1998)), Park et al. (*Analytical Chemistry* 75:6029-6033 (2003)), Hahn et al. (WO 2005/075683), Enzelberger et al. (U.S. Pat. No. 6,960,437) and Knapp et al. (U.S. Patent Application Publication No. 2005/0042639).

Many detection methods require a determined large number of copies (millions, for example) of the original DNA molecule, in order for the DNA to be characterized. Because the total number of cycles is fixed with respect to the number of desired copies, the only way to reduce the process time is to reduce the length of a cycle. Thus, the total process time may be significantly reduced by rapidly heating and cooling samples to process phase temperatures while accurately maintaining those temperatures for the process phase duration.

Accordingly, what is desired is a system and method for rapidly and accurately changing process temperatures in PCR processes.

SUMMARY

The present invention relates to systems and methods for determining and controlling the temperature of integrated thin film resistive heater elements in a microfluidic device for microfluidic thermal cycling.

In one aspect, the present invention provides a method for calibrating a pulse width modulation thin-film heater control system for an integrated thin-film device with a plurality of microfluidic channels, wherein each channel has at least one heater electrode. In one embodiment, the method includes: (a) applying electrical power to the at least one heater electrode in each channel; (b) measuring a voltage drop across each of the heater electrodes to determine individual electrode resistance values; (c) computing a heater power based on the individual heater electrode resistance values; (d) applying the heater power to the heater electrodes for a pre-determined calibration pulse time; (e) collecting heater electrode resistance measurements for a predetermined collection time at a predetermined sampling rate; (f) using the measurements to compute a thermal decay time constant; (g) computing an optimal pulse width modulation frequency based on the decay time information for each heater electrode in each channel; and (h) varying the duty cycle of the optimal pulse width modulation frequency for each heater electrode for controlling the temperature of each heater electrode.

In another aspect, the present invention provides a method for calibrating a pulse width modulation (PWM) thin-film heater control system to effect a biological reaction in a microfluidic device, wherein the microfluidic device includes a plurality of thin-film heaters that heat a plurality of microfluidic channels. In one embodiment, the method includes: (a) determining a thin-film heater resistance in between PWM energy cycles; (b) computing a microfluidic channel temperature based on the thin-film heater resistance; (c) applying a controlled current pulse to the thin-film heaters; (d) measuring a thermal decay time constant of the thin-film heaters after application of the controlled current pulse; (e) calculating an optimal PWM frequency for the thin-film heaters based on the time constant; and (f) adjusting the PWM frequency to said optimal frequency.

In another embodiment, the method includes the step of determining a thin-film heater resistance comprises measuring a voltage drop across the thin-film heater. The methods of the present invention are useful for analyzing a variety of biological reactions such as, for example, polymerase chain reaction and high resolution thermal melt.

In another aspect, a microfluidic device is provided that incorporates thin-film heaters within a plurality of microfluidic channels to effect a biological reaction with multiple steps each requiring a different temperature. In one embodiment, a method of controlling the microfluidic heaters of the microfluidic device with pulse width modulation includes: (a) generating a set of calibration data; (b) using the calibration data to generate a PWM control signal for the thin-film heaters designed to bring the heaters to the desired temperature for a first step in the biological process; (c) adjusting the PWM signal to achieve a temperature for an appropriate time required by the first step; and (d) adjusting the PWM signal to achieve the desired temperature for a second step in the PCR process.

In another embodiment, the method includes differentially sequencing the PWM signals to minimize current draw and power spiking on the system power supply. Other embodiments include differentially sequencing the PWM signals to achieve a multiplexed sequence among 3 or more microfluidic channels. In still other embodiments, the PWM signal is multiplexed between the plurality of thin-film heaters within the microfluidic channels.

In other embodiments, the method of generating a set of calibration data comprises: (a) applying electrical power to all heater electrodes; (b) measuring a voltage drop across each of the heater electrodes to determine individual electrode resistance values; (c) computing a nominal heater power based on the individual heater electrode resistance values; (d) applying the nominal heater power to the heater electrodes for a pre-determined calibration pulse time; (e) collecting heater electrode resistance measurements for a predetermined collection time at a predetermined sampling rate; (f) using the measurements to compute a thermal decay time constant; and (g) computing an optimal pulse width modulation frequency based on the decay time information.

In another aspect, the present invention provides a microfluidic device incorporating thin-film heaters within a plurality of microfluidic channels to effect a biological reaction. In one embodiment, the device includes a microfluidic chip comprising a first zone and a second zone wherein the first zone and the second zone include a plurality of microfluidic channels and a plurality of thin-film heaters disposed beneath said microfluidic channels. The microfluidic device further includes control circuitry configured to generate pulse width modulation control signals for each of the thin-film heaters in the first and second zones, wherein the control circuitry is configured to calibrate the PWM signals so that the PWM signals are optimized for each of the thin-film heaters.

In another embodiment, the control circuitry is configured to calibrate the PWM signals by: applying electrical power to all heater electrodes; measuring a voltage drop across each of the heater electrodes to determine individual electrode resistance values; computing a heater power based on the individual heater electrode resistance values; applying the heater power to heater electrodes for a pre-determined calibration pulse time; collecting heater electrode resistance measurements for a predetermined collection time at a predetermined sampling rate; using the measurements to compute a thermal decay time constant; and computing an optimal pulse width modulation frequency based on the decay time information.

In another embodiment, the control circuitry is configured to compute the heater power by using a look-up table to find the heater power associated with a particular resistance value. In yet another embodiment, the control circuitry is configured to produce multiplexed PWM control signals. In other embodiments, the control circuitry is configured to produce differential PWM control signals that alternate between a first set of PWM signals and a second set of PWM signals.

In another embodiment, the first zone of the microfluidic chip is used for conducting a polymerase chain reaction and the second zone is used for biological monitoring, such as, for example, thermal melt. The biological monitoring may also be end point PCR fluorescence. In some embodiments, the microfluidic chip is removable.

In another aspect, the present invention provides a method of controlling a microfluidic device that in includes a plurality of thin-film heaters that heat a plurality of microfluidic channels to effect a biological reaction. In one embodiment, the method includes: (a) measuring a thin-film heater resistance in between pulse width modulation energy cycles so as to measure the microfluidic channel temperature; (b) measuring a thermal decay time constant of the thin-film heaters after application of a controlled current pulse; and (c) adjusting the pulse width modulation frequency to be optimal for the thermal decay time constant of the thin-film heaters.

In another embodiment, the method includes: (a) providing control circuitry configured to generate pulse width modulation (PWM) control signals to drive the thin-film heaters; (b) differentially sequencing the pulse width modulation control signals to said thin-film heaters so as to minimize current draw and power spiking on a system supplying power to said microfluidic device. In some embodiments, the pulse with modulation control signals are differentially sequenced among 3 or more microfluidic channels. In other embodiments, the pulse with modulation control signals are differentially sequenced among two banks of parallel microfluidic channels.

In another aspect, the present invention provides a microfluidic device for performing biological reactions. In one embodiment, the microfluidic device includes: (a) a microfluidic chip comprising a first zone having a plurality of microfluidic channels and a second zone having a plurality of microfluidic channels, wherein the microfluidic channels in the first and second zones are in fluid communication, the microfluidic chip further comprising a thin-film heater in thermal communication with each of the microfluidic channels in the first and second zones; (b) a control system configured to independently control the temperature of each of the thin-film heaters using pulse width modulation (PWM) control signals that are optimized for each of the thin-film heaters.

In another embodiment, the control system provides PWM control signals to the thin-film heaters corresponding to the first zone configured to effect a polymerase chain reaction and wherein the control system provides PWM control signals to the thin-film heaters corresponding to the second zone configured to effect biological monitoring. In other embodiments, the control system includes a closed-loop control system configured to adjust the duty cycle of the PWM signal in order to maintain a desired temperature.

The above and other embodiments of the present invention are described below with reference to the accompanying drawings.

BRIEF DESCRIPTION OF THE DRAWINGS

The accompanying drawings, which are incorporated herein and form part of the specification, illustrate various embodiments of the present invention. In the drawings, like reference numbers indicate identical or functionally similar elements. Additionally, the left-most digit(s) of the reference number identifies the drawing in which the reference number first appears.

DETAILED DESCRIPTION OF PREFERRED EMBODIMENTS

Polymerase chain reaction (PCR) is one of the most common and critical processes in molecular diagnostics and other genomics applications that require DNA amplification. In PCR, target DNA molecules are replicated through a three phase temperature cycle of denaturation, annealing, and extension. In the denaturation step, double stranded DNA is thermally separated into single stranded DNA. In the annealing step, primers hybridize to single stranded DNA. In the extension step, the primers are extended on the target DNA molecule with the incorporation of nucleotides by a polymerase enzyme.

Figure 1:
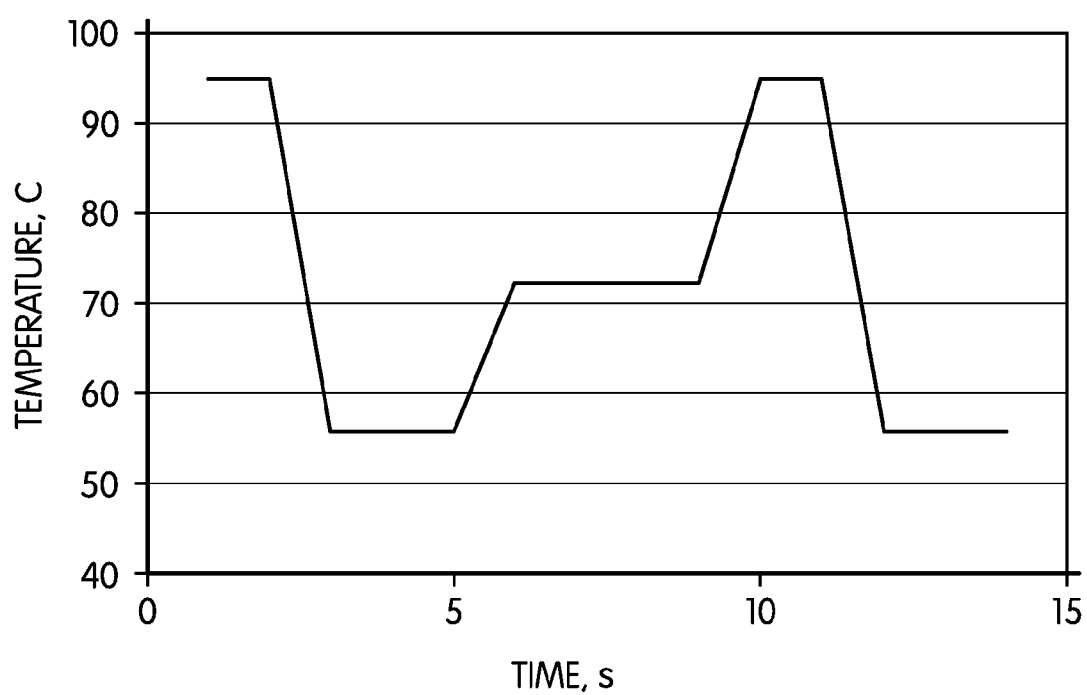
FIG. 1 depicts a graph illustrating a temperature versus time PCR profile.

Typical PCR temperatures are 95° C. for denaturation, 55° C. for annealing, and 72° C. for extension. The temperature at a step may be held for an amount of time from fractions of a second to several seconds, as shown in FIG. 1. In principle, the DNA doubles in amount at each cycle, and it takes approximately 20 to 40 cycles to complete a desired amount of amplification. To have good yield of target product, one has to control the sample temperatures at each step to the desired temperature for each step. To reduce the process time, one has to heat and cool the samples to desired temperature very quickly, and keep those temperatures for the desired length of time to complete the synthesis of the DNA molecules in each cycle. This can be accomplished using a microfluidic chip and thin-film heaters.

Figure 2:
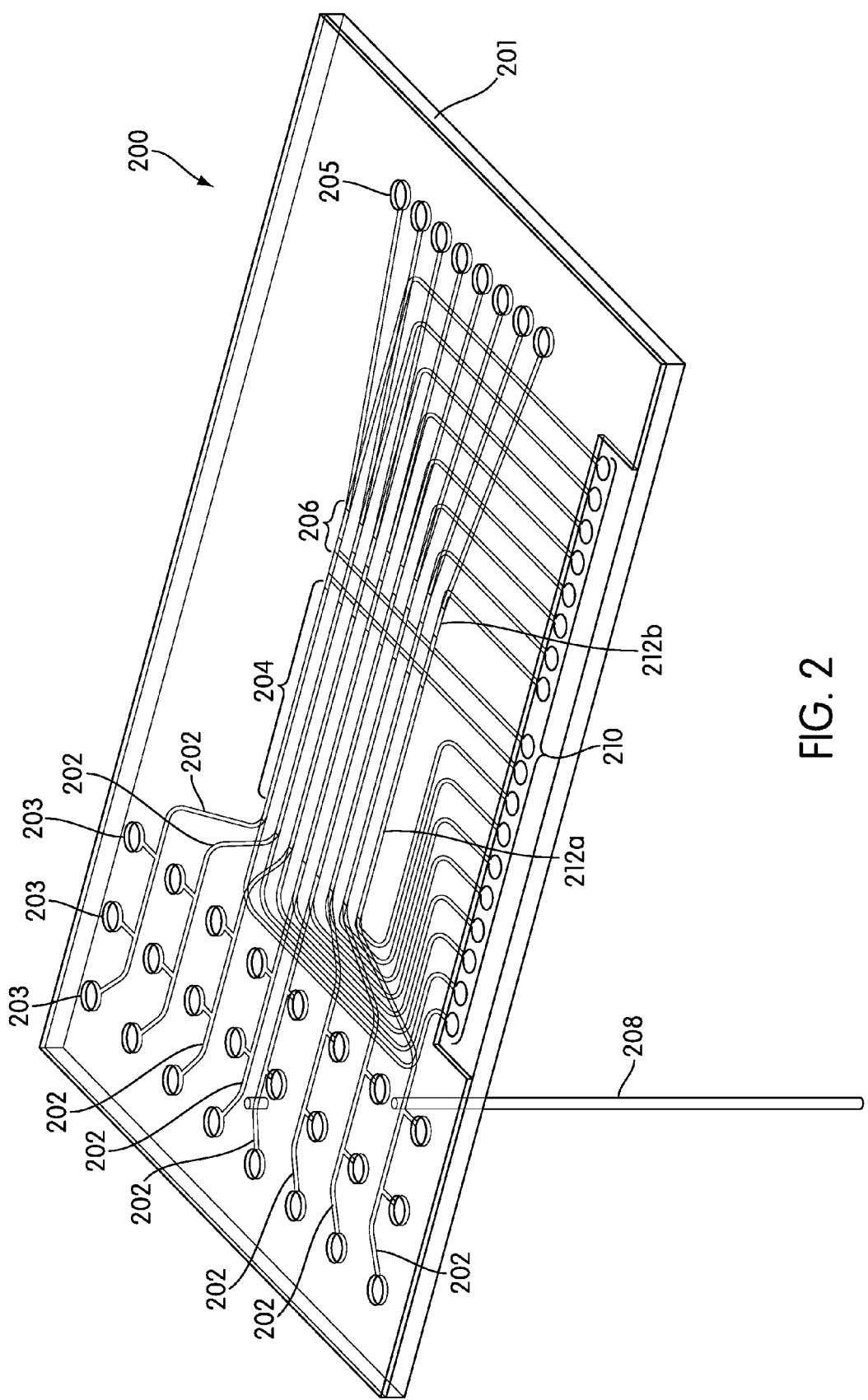
FIG. 2 depicts a perspective view of a microfluidic device embodying aspects of the present invention.
Figure 3:
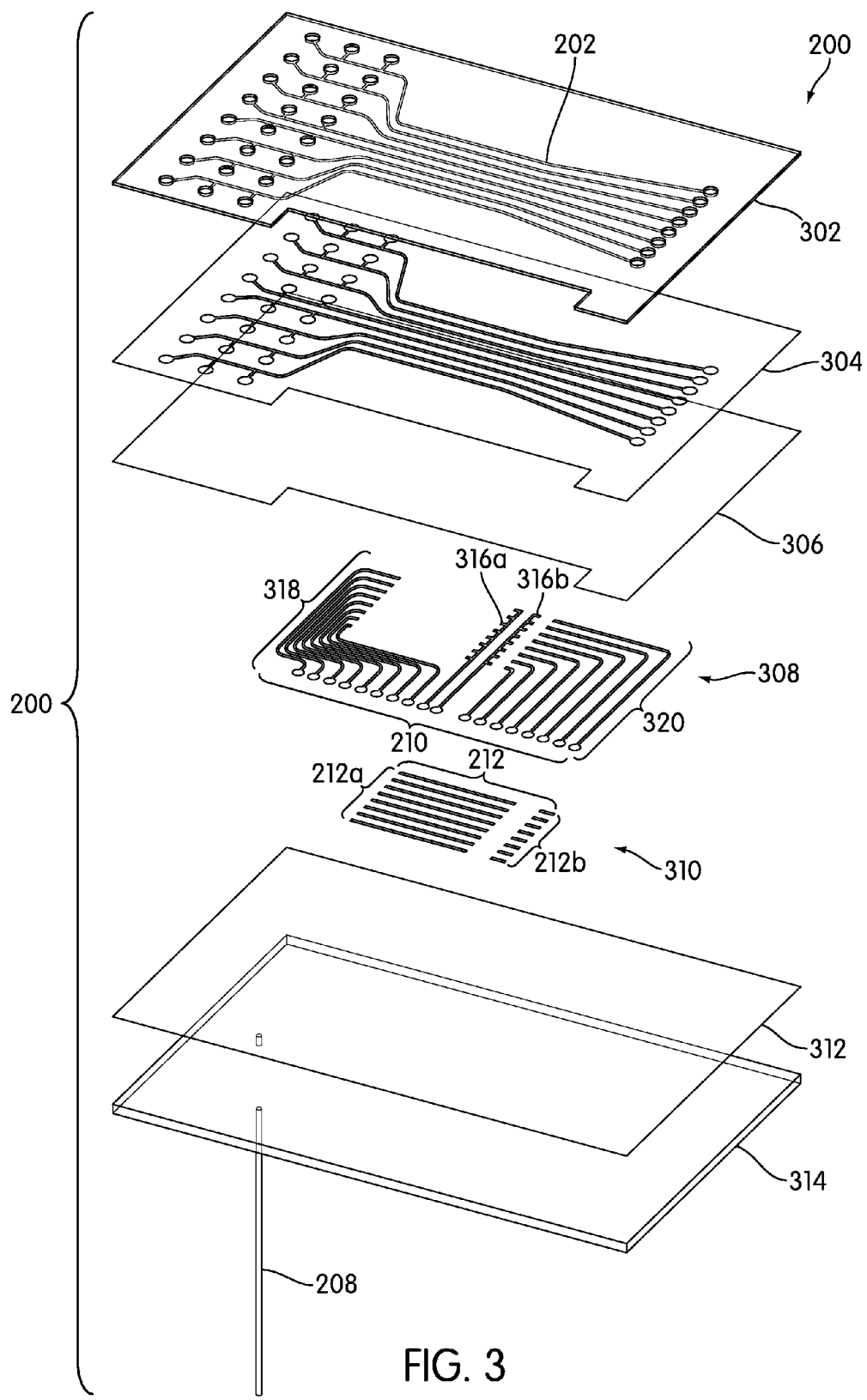
FIG. 3 depicts an exploded perspective view of the microfluidic device of FIG. 2.

As shown in FIGS. 2 and 3, a microfluidic device 200 embodying aspects of the present invention may comprise several microfluidic channels 202 extending across a substrate 201. Each channel 202 may include one or more inlet ports 203 (the illustrated embodiment shows three inlet ports 203 per channel 202) and one or more outlet ports 205 (the illustrated embodiment shows one outlet port 205 per channel 202). Each channel may be subdivided into first portion extending through a PCR thermal zone 204 (as described below) and a second portion extending through a thermal melt zone 206 (as described below). A sipper 208 can be used to draw liquid into the several microfluidic channels 202.

The microfluidic device 200 further includes heater elements in the form of thin film resistive heaters 212. In one embodiment, a heater element 212 is associated with each microfluidic channel 202 and may be located beneath the microfluidic channel 202. Each heater element 212 comprises two heater sections: a PCR heater 212*a* section in the PCR zone 204 and a thermal melt heater section 212*b* in the thermal melt zone 206. In one embodiment, heater electrodes 210 provide electrical power to the several thin-film heaters 212*a* and 212b. In the embodiment shown in FIG. 2, the microfluidic device has separate electrical circuits and contacts for controlling independently the temperature of each microfluidic channel in the PCR and thermal melt zones 204, 206. In this illustrated embodiment, each area has eight microfluidic channels and eight heaters, with eight individual contacts per zone plus a common electrical contact for each zone. Embodiments having other than eight channels are contemplated as well.

As shown in FIG. 3, the microfluidic device 200 can comprise several different layers. The microfluidic channels 202 can be etched in a channel layer 302. According to some embodiments, the channel layer 302 may comprise fused silica and have a thickness of about 200 μm. Of course, other layer thicknesses may be used as well. A polymer glue layer 304 may connect the channel layer 302 to a protective layer 306. According to some embodiments of the present invention, the protective layer is formed from $SiO_2$ and has a thickness of approximately 1-2 μm. Glue layer 304 may comprise sheet material with features formed therein corresponding to the channels 202 and ports 203, 205. Alternative adhesive layers may be formed by UV curable optical adhesives such as, for example, Norland NOA 72.

Electrical conductor layer 308 may comprise a plurality of heater electrodes 210 connected to the various thin-film heaters 212*a* and 212*b* of thin-film heater layer 310. Heater electrodes 210 may include PCR section leads 318, a PCR section common lead 316*a*, thermal melt section leads 320, and a thermal melt section common lead 316*b*. According to one embodiment of the present invention, one of the PCR section leads 318 is connected to one end of each of the thin-film PCR heaters 212*a*. A PCR common lead 316*a* is connected to the other end of each of the PCR heaters 212*a*. Similarly, one of the thermal melt section leads 320 and thermal melt section common lead 316*b* is connected to either end of each thermal melt heater 212*b*. While FIG. 3 shows the electrical conductor layer 308 and the heater layer 310 as separate layers, it would be understood by one of ordinary skill in the art that they could also comprise the same layer.

According to some embodiments of the present invention, the thin-film heater layer can be resistive materials of Pt, Al, $Al_2N_3$, Ni, ITO, Ni/chromium, etc.

In one embodiment, a platinum thin-film heater is used with deposition thickness in the range of approximately 10 to 5000 Angstroms, or more preferably within the range of approximately 50 to 1000 Angstroms. Typical heater film resistance values range from approximately 200 to 800 μΩ-cm, or approximately 20 to 1000 Ω total resistance, or preferably approximately 50 to 250 Ω total resistance. The exact composition of thin-film heater material can be optimized by taking into account the peak drive currents, overall trace resistances achievable, and design stability/durability.

Another alternate embodiment could incorporate the thin-film heater resistor layer and a separate nearby resistor trace for measuring the nearby heat by the TCR characteristics of the resistor layer.

The heater electrodes 210, including PCR section leads 318, thermal melt section leads 320, and common leads 316*a* and 316*b*, can be composed of various materials ordinarily used as thin-film electrodes such as, for example, Al, Ag, Au, Pt, Cu, etc. Electrode formation can be, for example, by evaporation with a desired shape, size, and thickness. The electrodes can also be prepared by conventional sputtering process such as, for example, in an Ar gas atmosphere.

In one embodiment, a protective layer 312 separates the thin film heater layer 310 from the substrate layer 314. The protective layers 306 and 312 may be made from $SiO_2$ and can be prepared by conventional plasma CVD, or sputtering. The $SiO_2$ thickness can range from approximately 1-3 μm. A film layer made of Si:N can be formed by conventional plasma CVD. In one embodiment, the protective layer facilitates microchannel biocompatibility to enable efficient PCR processes by isolating the reaction channel from the thin-film heaters 212*a* and 212*b* and the heater electrodes 210.

Figure 4:
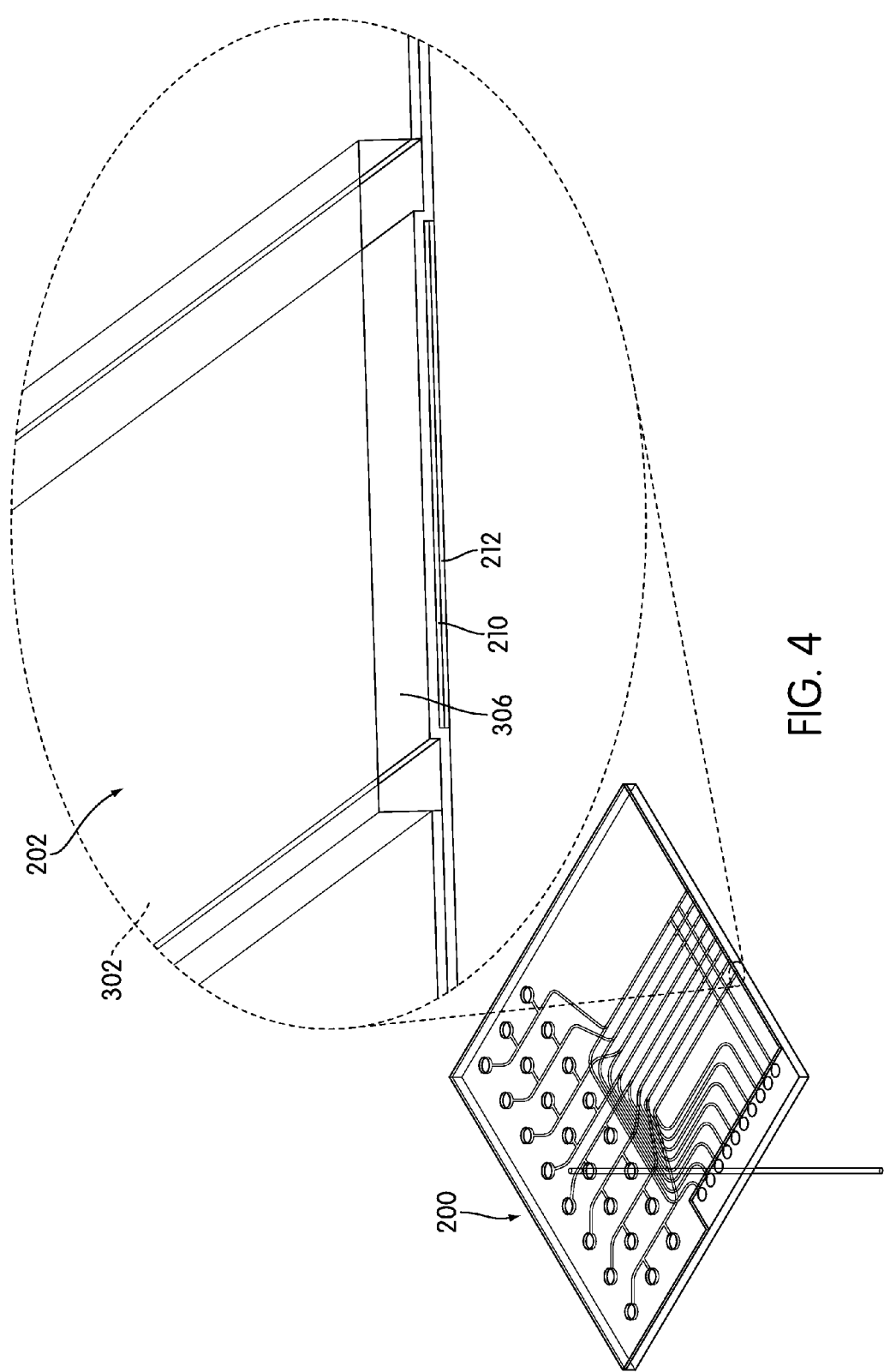
FIG. 4 depicts a partial perspective view of the microfluidic device of FIG. 2 with a portion of the device shown enlarged.

FIG. 4 shows a partial view of microfluidic device 200 showing a single channel 202 in detail. As illustrated in FIG. 4, the single channel 202 includes the channel layer 302, the heater electrodes 210, thin film heater 212 and protective layer 306. The microfluidic channel and thin film heater can be created having suitable dimensions for performing PCR and high resolution thermal melt reactions. In one exemplary embodiment, the microfluidic channel 202 dimensions can be approximately 10 μm×180 μm and the thin-film heater 212 beneath the microfluidic channel 202 can be approximately 150 μm wide at the bottom of the channel. Other microfluidic channel dimensions can be used as well such as, for example, approximately 10 μm×300 μm, or more. Other thin film heater dimensions could be used such as, for example, from approximately 30 μm wide to 300 μm wide (i.e. the full width of the channel in one embodiment), or more.

FIG. 4 shows a portion of the device 200 at which a thin-film heater 212 is overlapped by one of the electrodes 210. Other embodiments may also include dual thin-film heaters running down the channel in parallel. Such a design would be optimized at normalizing the thermal temperature distribution within the microfluidic channel 202.

Figure 5:
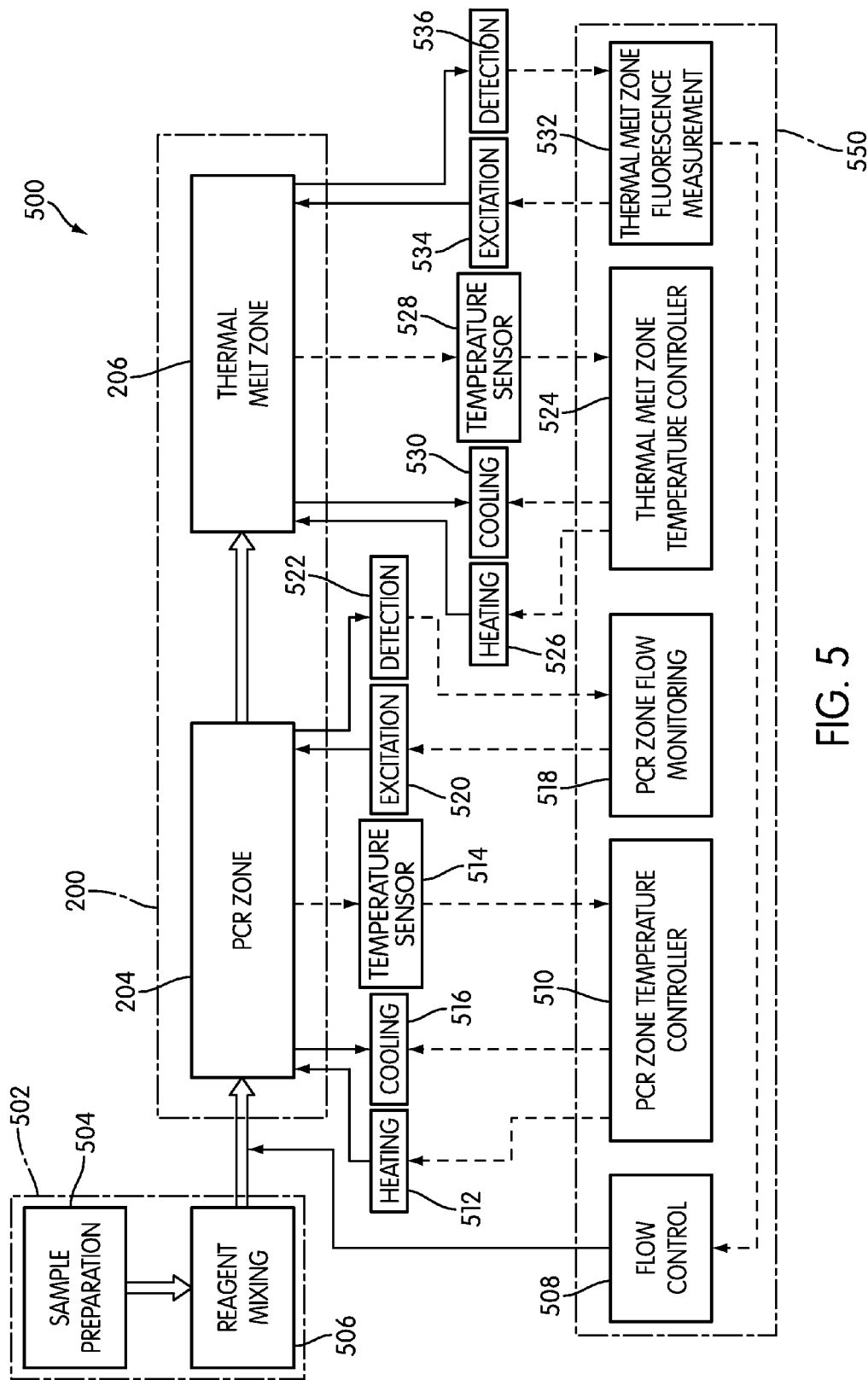
FIG. 5 depicts a block diagram illustrating the various functional and control regions of a microfluidic device.

Referring now to FIG. 5, a functional block diagram of a system 500 for using a microfluidic device 200 is illustrated. The DNA sample is input in the microfluidic chip 200 from a preparation stage 502. The preparation stage 502 may comprise appropriate devices for preparing the sample 504 and for adding one or more reagents 506 to the sample. Once the sample is input into the microfluidic chip 200, e.g., at an input port 203 or via sipper tube 208, it flows through a channel 202 into the PCR zone 204 where PCR takes place. That is, as explained in more detail below, as the sample flows within a channel 202 through the PCR zone 204, it is exposed to the temperature profile as shown in FIG. 1a a plurality of times to effect PCR amplification. Next, the sample flows into the thermal melt zone 206 where a high resolution thermal melt process occurs. Flow of sample into the microfluidic chip 200 can be controlled by a flow controller 508. A control system 550 may comprise a flow controller 508, a PCR zone temperature controller 510, a PCR flow monitor 518, a thermal melt zone temperature controller 524, and a zone fluorescence measurement system 532.

The temperature in the PCR zone 204 can be controlled by the PCR zone temperature controller 510. The PCR zone temperature controller 510, which may be a programmed computer or other microprocessor, sends signals to the heater device 512 (e.g., a PCR heater 212a) based on the temperature determined by a temperature sensor 514 (such as, for example, an RTD or thin-film thermistor, or a thin-film thermocouple thermometer). In this way, the temperature of the PCR zone 204 can be maintained at the desired level. According to some embodiments of the present invention, the PCR zone 204 may also be cooled by a cooling device 516 (for example, to quickly bring the channel temperature from 92° C. down to 55° C.), which may also be controlled by the PCR zone temperature controller 510. In one embodiment, the cooling device 516 could be a peltier device, heat sink or forced convection air cooled device.

The flow of sample through the microfluidic channels 202 can be measured by a PCR zone flow monitoring system 518. In one embodiment, the flow monitoring system can be a fluorescent dye diffusion imaging and tracking system illustrated in U.S. patent application Ser. No. 11/505,358, incorporated herein by reference. According to one embodiment of the present invention, the channels in the PCR zone can be excited by an excitation device 520 and light fluoresced from the sample can be detected by a detection device 522. An example of one possible excitation device and detection device forming part of an imaging system is illustrated in U.S. patent application Ser. Nos. 11/606,006 and 11/505,358, incorporated herein by reference.

The thermal melt zone temperature controller 524, e.g. a programmed computer or other microprocessor, can be used to control the temperature of the thermal melt zone 206. As with the PCR zone temperature controller 510, the thermal melt zone temperature controller 524 sends signals to the heating component 526 (e.g., a thermal melt heater 212b) based on the temperature measured by a temperature sensor 528 which can be, for example an RTD or thin-film thermocouple. Additionally, the thermal melt zone 206 may be independently cooled by cooling device 530. The fluorescent signature of the sample can be measured by the thermal melt zone fluorescence measurement system 532. The fluorescence measurement system 532 excites the sample with an excitation device 534, and the fluorescence of the sample can be detected by a detection device 536. An example of one possible fluorescence measurement system is illustrated in U.S. patent application Ser. Nos. 11/606,006 and 11/505,358, incorporated herein by reference.

In accordance with aspects of the present invention, the thin film heaters 212 function as both heaters and temperature detectors. Thus, in one embodiment of the present invention, the functionality of heating element 512 and 526 and temperature sensors 514 and 528 can be accomplished by the thin film heaters 212.

Figure 6:
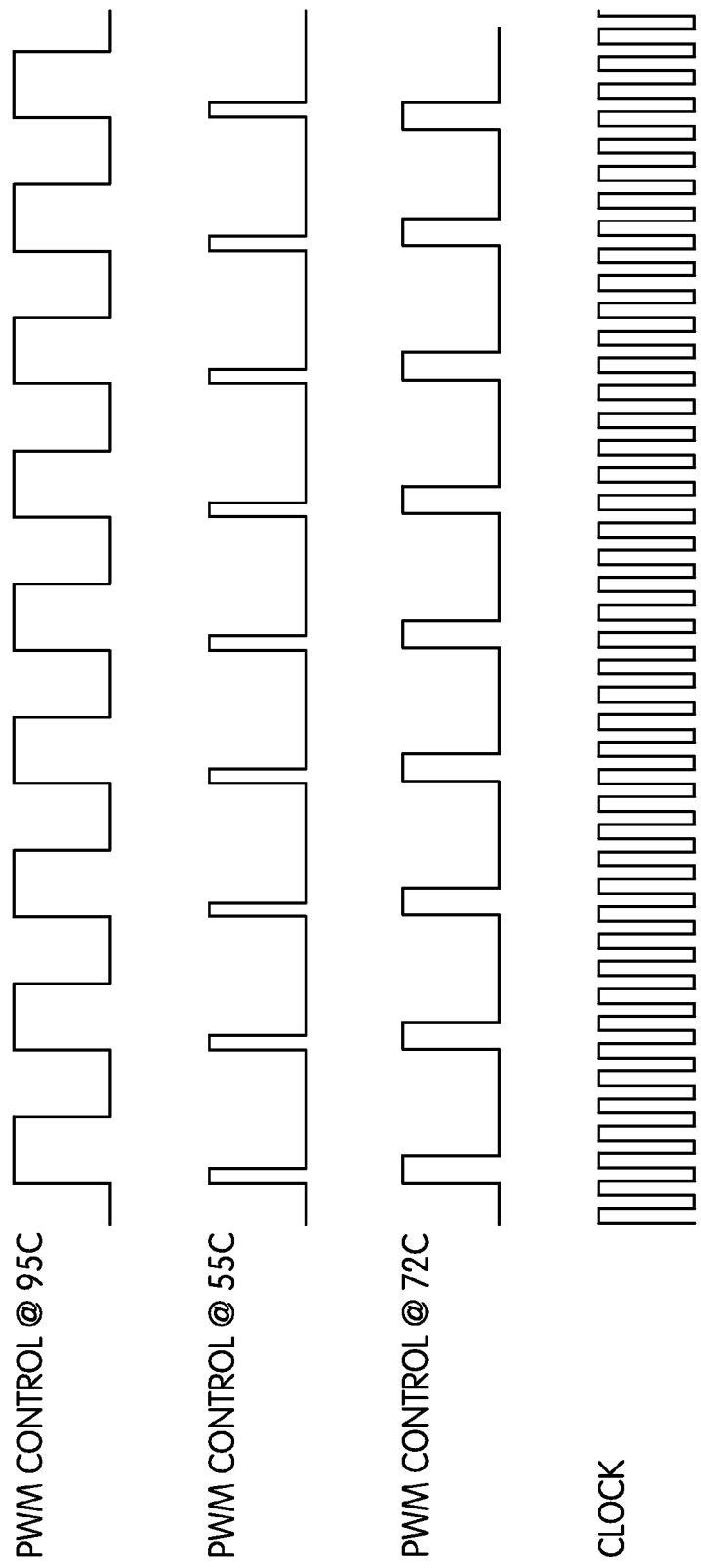
FIG. 6 depicts representative pulse width modulation (PWM) control profiles for achieving various temperatures in the resistive heater electrodes of the microfluidic device.

In one embodiment, the system 500 sends power to the thin-film heaters 212a and/or 212b, thereby causing them to heat up, based on a control signal sent by the PCR zone temperature controller 510 or the thermal melt zone temperature controller 524. The control signal can be a pulse width modulation (PWM) control signal, as shown in FIG. 6. It is advantageous to use a PWM signal to control the heaters 212, because with a PWM control signal, the same voltage potential across the heaters may be used for all of the various temperatures required. As shown in FIG. 6, the desired temperature for the heaters is reached by changing the duty cycle of the control signal. For example, the duty cycle of the control signal for achieving 95° C. in a PCR heater might be about 50% as shown in the first curve in FIG. 6. As the desired temperature decreases, so does the duty cycle. For example, when the desired temperature is 72° C., the duty cycle might be around 25% as shown in the third curve of FIG. 6. When the desired temperature is 55° C., the duty cycle might be only around 10%, as shown in the second curve of FIG. 6.

Figure 7:
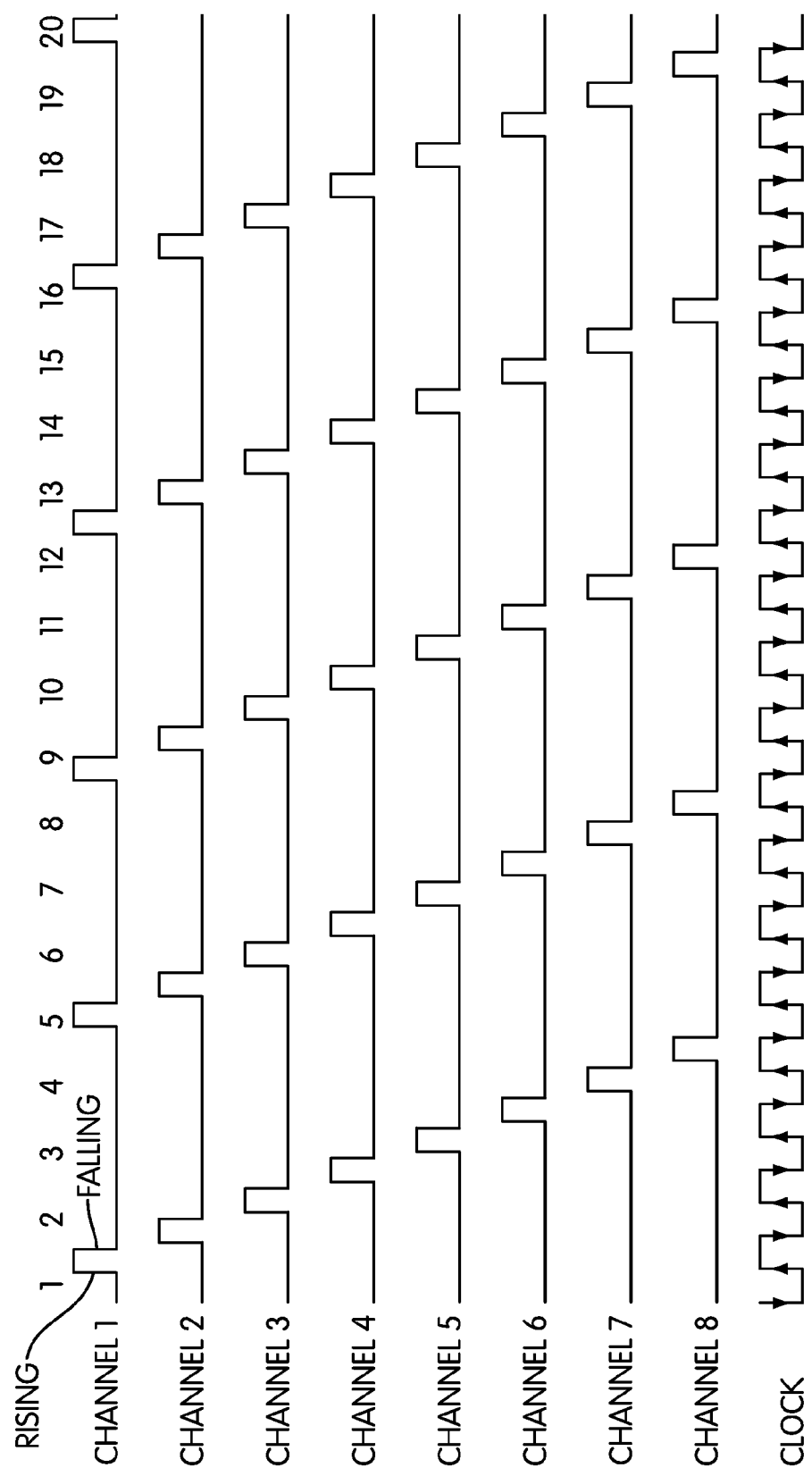
FIG. 7 depicts PWM profiles for an eight-channel microfluidic device, wherein the eight resistive heater electrodes are electrically driven in a multiplexed sequence.
Figure 8:
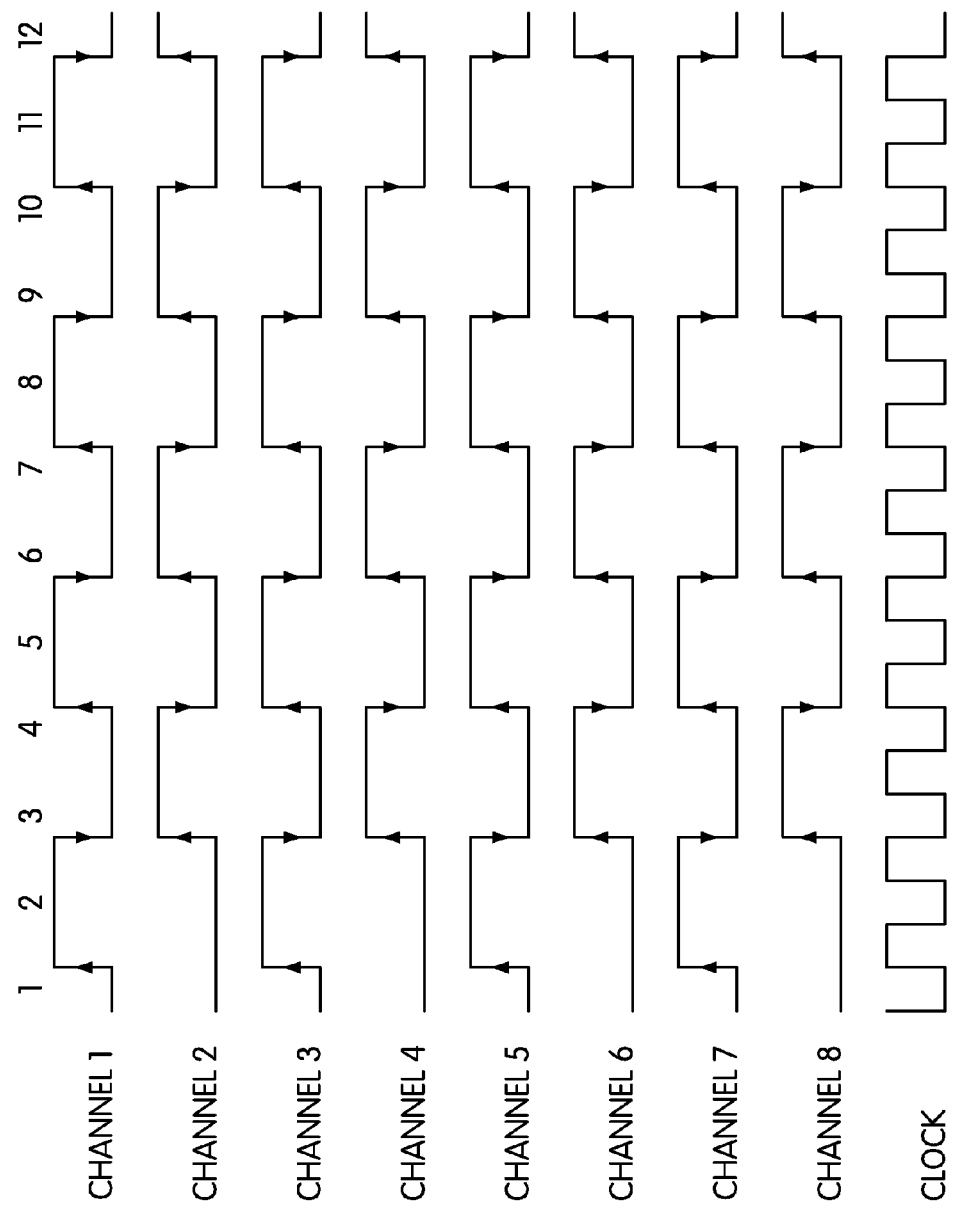
FIG. 8 depicts PWM profiles for a differential drive method for electrically driving microfluidic thin film resistive heaters.

According to one embodiment of the present invention, each thin-film heater 212a or 212b can be independently controlled. Independent control of the thin-film heaters permits the various heaters to be supplied with different amounts of power which may be desired to maintain the desired set temperature. For instance, in a non-limiting example, the edge-most heaters of the device 200 may require more power than the inner most heaters in order to maintain the same temperature. Individual control of the heaters also has the advantage of allowing the heaters to be multiplexed, as illustrated in FIGS. 7 and 8. Multiplexing the thin-film heaters 212 allows for a balanced energy drain from the power source and mitigates heat build up in the substrate 314.

Figure 9:
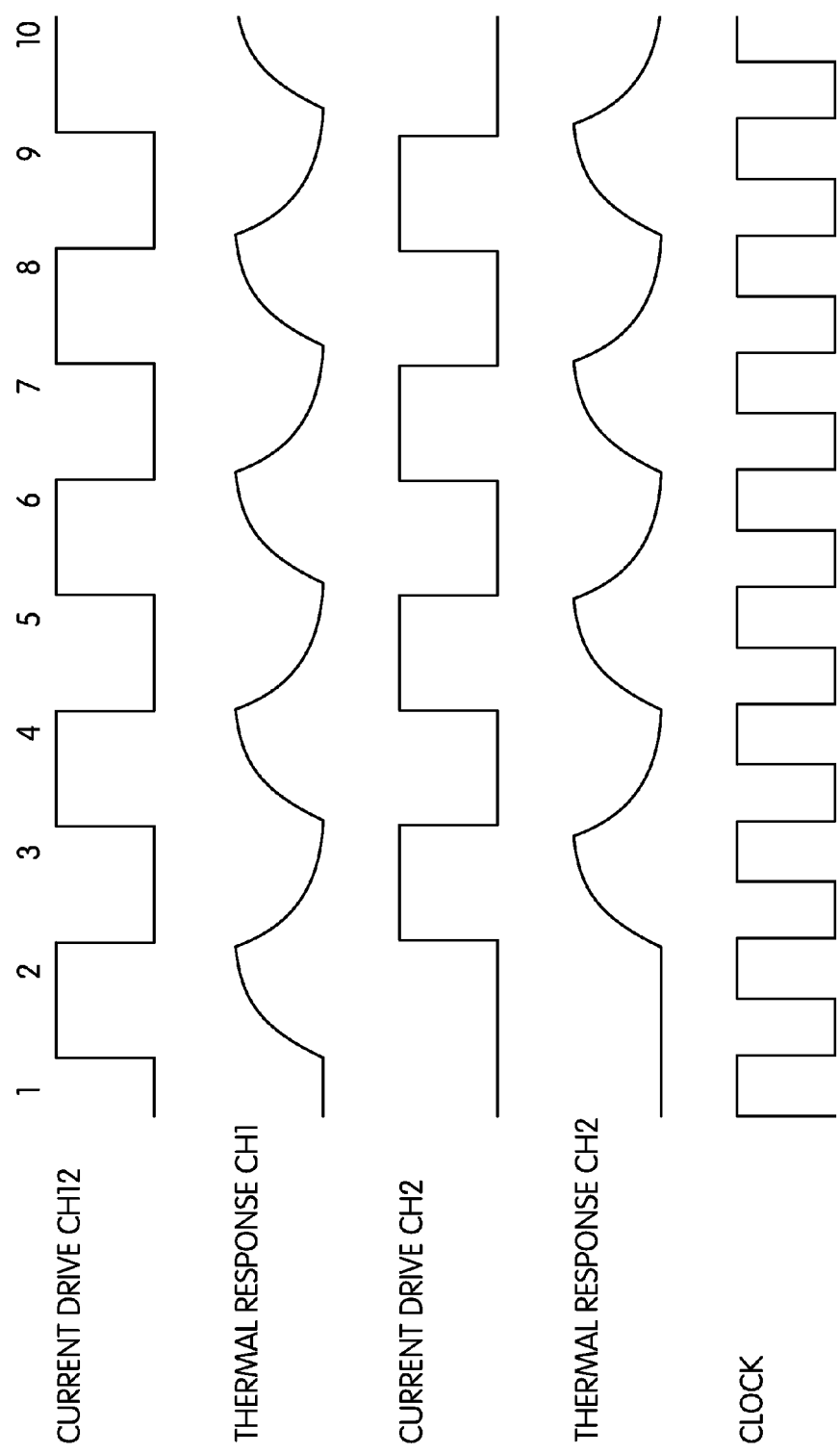
FIG. 9 depicts a representative thermal response to PWM drive signals of two microfluidic heater channels.

As shown in FIG. 7, the heater signals may be multiplexed one after the other in succession. For instance, the falling edge of the control pulse for microfluidic channel 1 may occur at the same time or after the rising edge for channel 2's control pulse, and the rising edge for channel 3's control pulse could occur at the same time or after the falling edge of channel 2's control pulse and so on. In another embodiment, as shown in FIG. 8, several of the channels may be driven at the same time. For instance, FIG. 8 shows channels 1, 3, 5 and 7 being driving at the same time and channels 2, 4, 6 and 8 being driven at the same time. While a 50/50 duty cycle is shown for illustration purposes only, actual duty cycles would change based on the desired temperature. FIG. 9 shows the representative thermal response to the differential drive method whereby the CH1 and CH2 channels are thermally out of phase. Such a method is aimed at distributing the thermal energy with PWM so that the base temperature rise of the substrate chip material is minimized.

Figure 10:
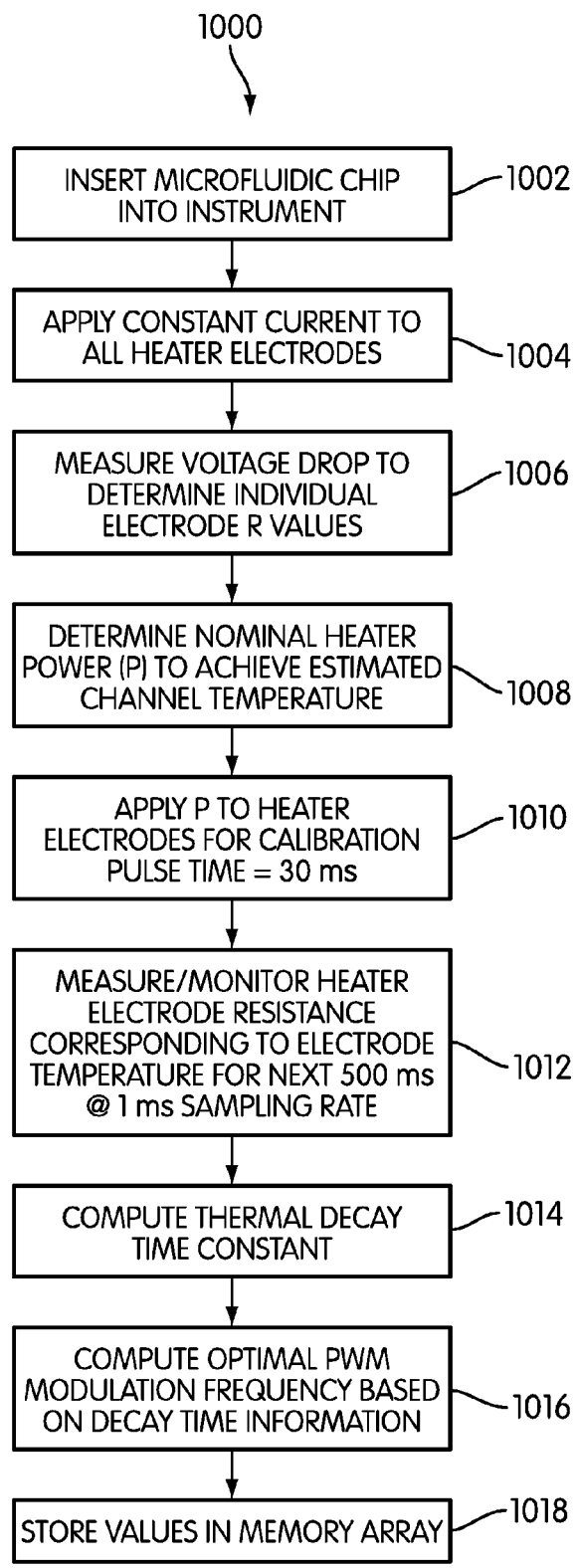
FIG. 10 depicts a flow chart showing a heater calibration method.

Individual microfluidic devices 200 can vary from chip to chip. Thus, to improve the temperature set-point accuracy for each chip, the control system for the microfluidic device 200 can be calibrated. As shown in FIG. 10, according to one embodiment of the present invention, a method 1000 for calibrating a microfluidic device prior to use is provided. The microfluidic device is first inserted into the system 500 at step 1002. The control system 550 then applies a constant current to all of the heater electrodes 210 at step 1004. Next, at step 1006, the voltage drop across each of the thin-film heaters 212 can then be measured to determine individual resistance (R) values. Using the individual R values, a nominal heater power (P) can be determined to achieve the required channel temperatures for each microfluidic channel 202 at step 1008. Next, the nominal power P is applied to each of the thin-film heaters for a predetermined time at step 1010. In one embodiment, the predetermined time can be from approximately 5 µs to 30 ms, and is preferably approximately 100 µs.

The temperature of the thin-film heater 212a or 212b is next monitored by measuring the changing resistance as the thin-film heater 212 cools at step 1012. From the data collected at step 1012, a thermal decay time constant for each thin film heater 212 can then be calculated at step 1014 and an optimal PWM modulation frequency can be calculated based on the thermal decay time constant at step 1016. The thermal decay time constant may be determined, for example, by taking two or more temperature readings separated in time after heating power is stopped. With the heating power off, the temperature of the heater will begin to drop. The initial rate of temperature decay, in terms of degrees per unit time, may be calculated, for example, from two data points through simple algebra, through three or more data points by linear regression, or to many data points through a more complex model through curve fitting. Then, the digital drive signal to the heater should be adjusted to be at a high enough frequency to result in an acceptably small drop in temperature between consecutive pulses. The thermal decay time constant values are then stored in memory at step 1018. The calibration method can be used to calibrate the control system 550 for both the PCR zone 204 and the thermal melt zone 206.

In one embodiment, the calibration pulse time is between approximately 10 µs to 10 ms, more preferably between approximately 200 µs to 2 ms, and most preferably approximately 500 µs. The heater electrode resistance measurement collection time is between approximately 1 µs to 1000 µs, more preferably between approximately 10 µs to 100 µs, and most preferably approximately 25 µs. The sampling rate for collecting the heater electrode resistance measurements is between approximately 0.1 µs to 1000 µs, more preferably between approximately 1 µs to 10 µs, and most preferably approximately 2.5 µs.

Figure 11:
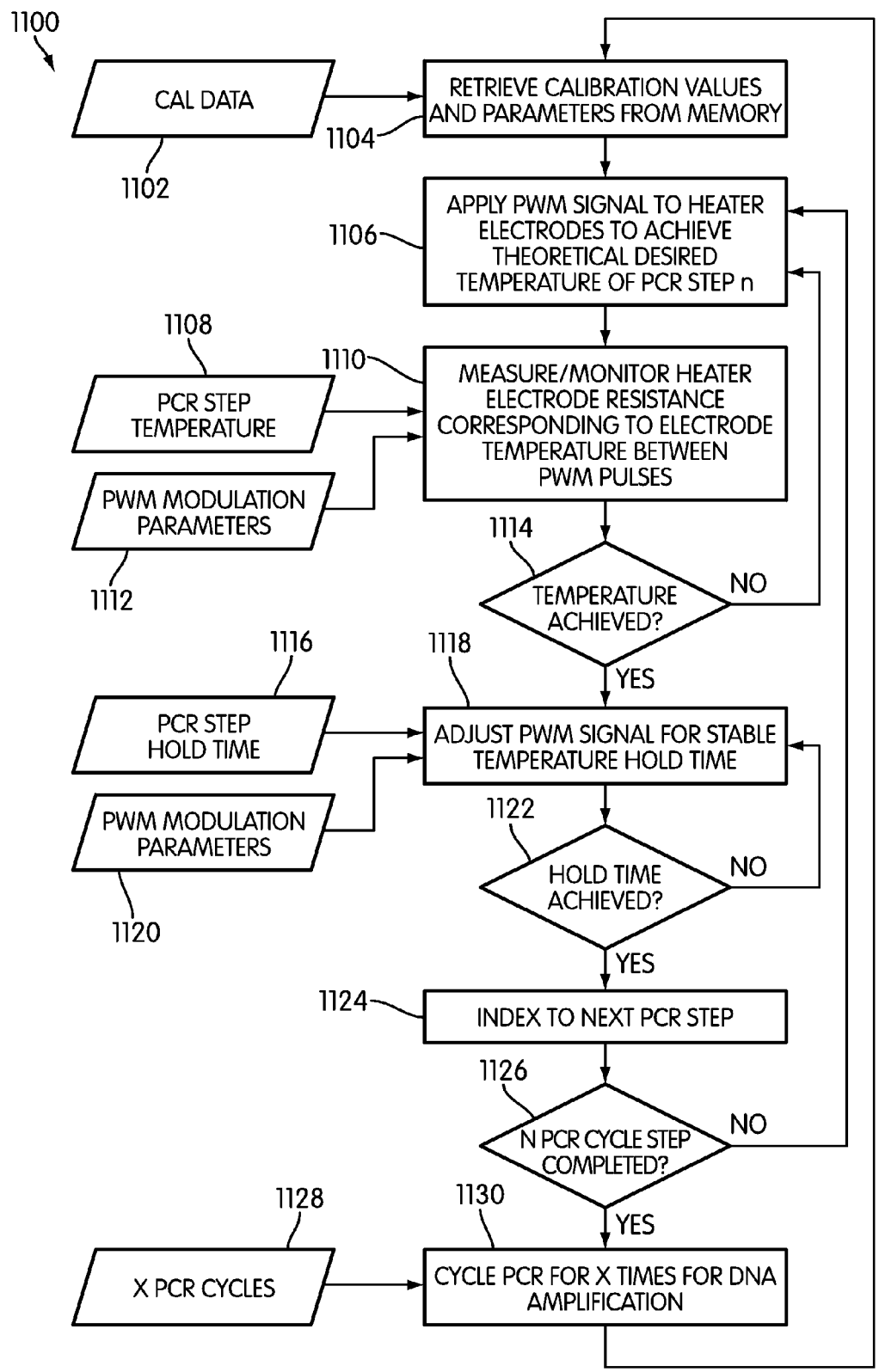
FIG. 11 depicts a flow chart showing a PWM control method whereby calibration values are stored and utilized to compute optimum PWM conditions.

FIG. 11 illustrates a method of temperature cycling 1100 to achieve PCR using calibration data collected using method 1000. Calibration data 1102 is retrieved from memory at step 1104. At step 1106, the appropriate PWM signal (based on the calibration data) is next applied to each of the heater electrodes to achieve the desired temperature of the current PCR step. At step 1110, the temperature of the heaters is measured and compared to the desired temperature for the current PCR step 1108 and the PWM modulation parameters 1112. According to one embodiment, the temperature can be measured between PWM pulses as described below. At step 1114, it is determined whether the appropriate temperature has been achieved. If it has not been achieved, then the method returns to step 1106. If it has been achieved, then the PWM signal is adjusted to maintain the temperature for the appropriate hold time for the current PCR step at step 1118 using the PCR step hold time 1116 and the PWM modulation parameters 1120. At step 1122, the method determines whether the appropriate hold time has been achieved. If the hold time has not been achieved, then the method returns to step 1118. If the appropriate hold time has been achieved, then, at step 1124, the method indexes to the next PCR step. At step 1126, it is determined whether an entire PCR cycle has been completed. If not, then the method returns to step 1106. If it has been completed, then the method determines whether the appropriate number of cycles have been completed and returns to step 1104 if not.

In addition to heating the microfluidic channel 202, thin film heaters 212a and 212b can measure the temperature of the microfluidic channels. To do so, the thin film heaters 212a and/or 212b are preferably constructed from a material with an electrical resistance that changes with temperature, such as platinum, Al, ITO, Cu, Ni and Ni alloys. Thus, temperature can be derived from the determined resistance of the heater. The measured temperature can be used in a closed loop feedback controller.

Figure 12:
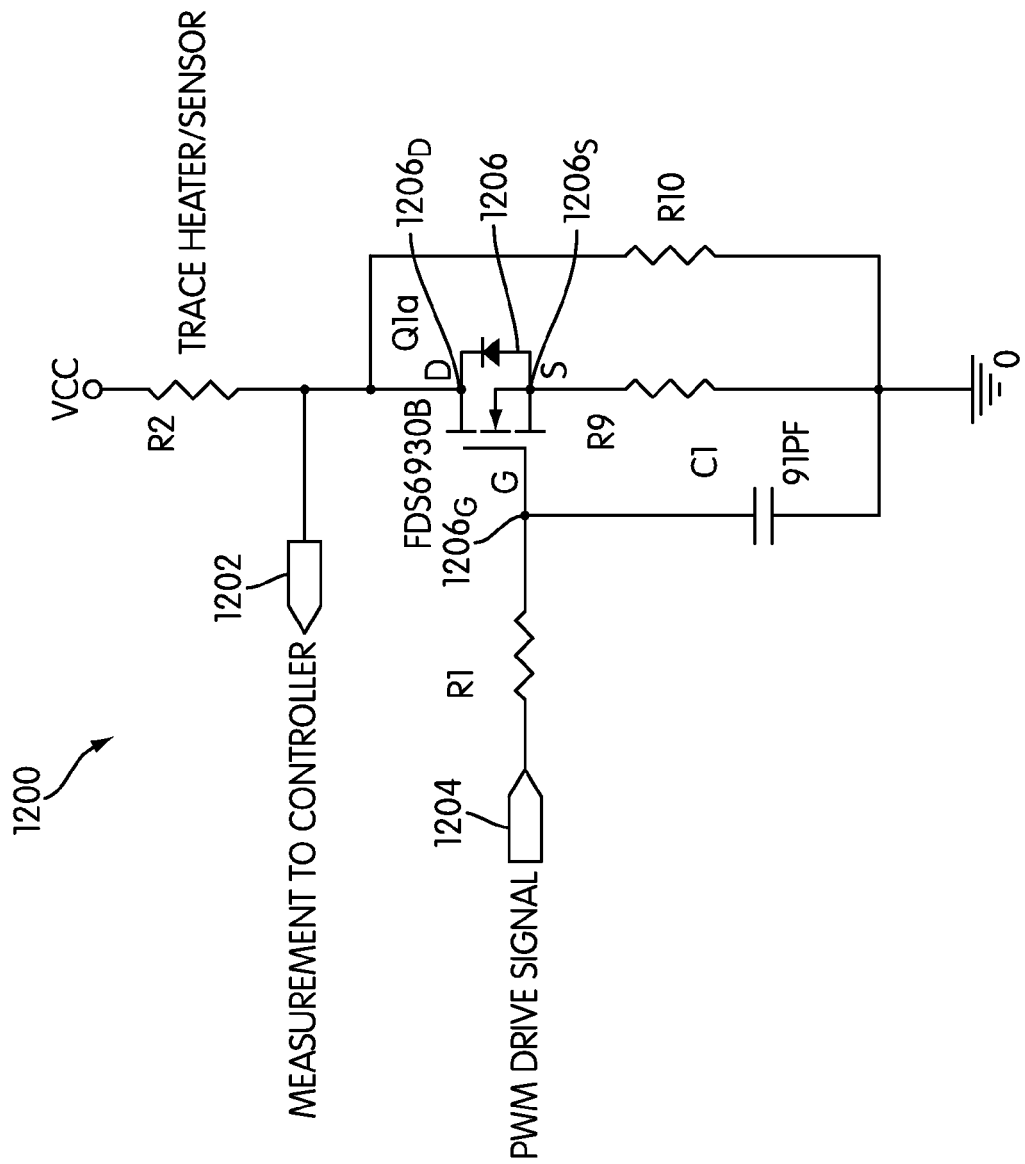
FIG. 12 depicts a circuit enabling temperature measurements in a resistive heater electrode during both the power-off and power-on portions of a PWM duty cycle.

In one embodiment, the power delivered to the thin-film heaters 212 is modulated using a digital transistor switch instead of an analog voltage. As illustrated in FIG. 12, digital transistor switch 1206 may be a FET, and preferably may be a MOSFET. The control system varies the duty cycle (i.e., pulse width) of the drive signal to regulate power delivered to the thin-film heaters. When the transistor 1206 is ON, the control circuit can measure the current delivered to the heat trace R2 (comprising the PCR or thermal melt leads 318 or 320, a thin film heater 212a or 212b, and a common lead 316a or 316b and represented as R2 in FIG. 12). By knowing the current and voltage across the trace R2, control system 550 can calculate the impedance of R2. Next, the control system can use a formula (e.g., Callendar-Van Dusen) to convert the impedance value to a temperature value so the control system 550 can move and hold the temperature as required for the PCR assay.

It may, however, also be desirable to measure the current when the transistor is OFF. This is because when the transistor is in the ON state the thin-film heaters 212 heat up very rapidly, and the thin-film heaters 212 may be several degrees hotter than the fluid in the microfluidic channels 202. If the system overshoots the desired temperature and the water forms micro bubbles in the channel, the control system has difficulty because there is an insulating gas layer between its sensor and the load which causes a delay in feedback control. Another problem with the gas bubble is it has the potential to greatly expand causing flow to be uncontrollable in the microchannels.

Thus, in accordance with another aspect of the present invention, an improved design allows temperature measurement when the transistor is in both the OFF and ON states. In one embodiment, this can be accomplished by having a small current flowing through R2 even when the transistor is OFF. A drive system for permitting temperature measurement when the transistor is in both the OFF and ON states according to one embodiment of the present invention is illustrated in FIG. 12. In FIG. 12, a schematic of the PWM driver and measurement circuit 1200 is shown in which the transistor 1206 is connected to R2, which represents the combined resistance of the thin-film heaters 212a or 212b and the leads connected to it (i.e. 316a and 318 or 316b and 320). The voltage drop across R2 can be measured at measurement node 1202. The PWM drive signal is sent to the gate of the transistor 1206$_G$ at drive signal node 1204. A large value resistor R10 short circuits the drain 1206$_D$ and the source 1206$_S$. Preferably, R10 will be much larger (e.g., an order of magnitude or more) than R2. When the transistor 1206 is ON, then current will flow through R2, substantially as normal, and the voltage drop across R2 can be measured at measurement node 1202. The voltage drop across R2 can also be measured when the transistor 1206 is in the OFF state because of large value transistor R10 will allow a smaller current to flow through R2.

Due to the small current resulting from the large value of R10, the self heating of R2 will be small, so the temperature measured by the trace R2 will be close to the temperature of the fluid in the channel. The control system 550 can be configured to know when the transistor is ON and OFF, so it can use two different formulas to calculate the temperature. For instance, when the transistor is ON, R9 and transistor 1206 are in series and together are in parallel with R10, so the formula for calculating the resistance of R2 is:

$$R_2 = \frac{R_{(9+RdsON)//10}(V_{CC} - V_{measured})}{V_{measured}} \qquad \text{Equation 1}$$

where $R_{(9+RdsON)//10}$ represents the equivalent resistance of R10, R9 and the resistance of the transistor 1206.

When the transistor is OFF, R10 is in series with R2, so the formula is:

$$R_2 = \frac{R_{10}(V_{CC} - V_{measured})}{V_{measured}} \qquad \text{Equation 2}$$

where $V_{measured}$ is measured at node 1202.

From the resistance of trace R2, the temperature of R2 can be determined by, e.g., applying the Callendar-Van Dusen equation, and the temperature of R2 can be used in a control loop for regulating power to the heater.

Figure 13:
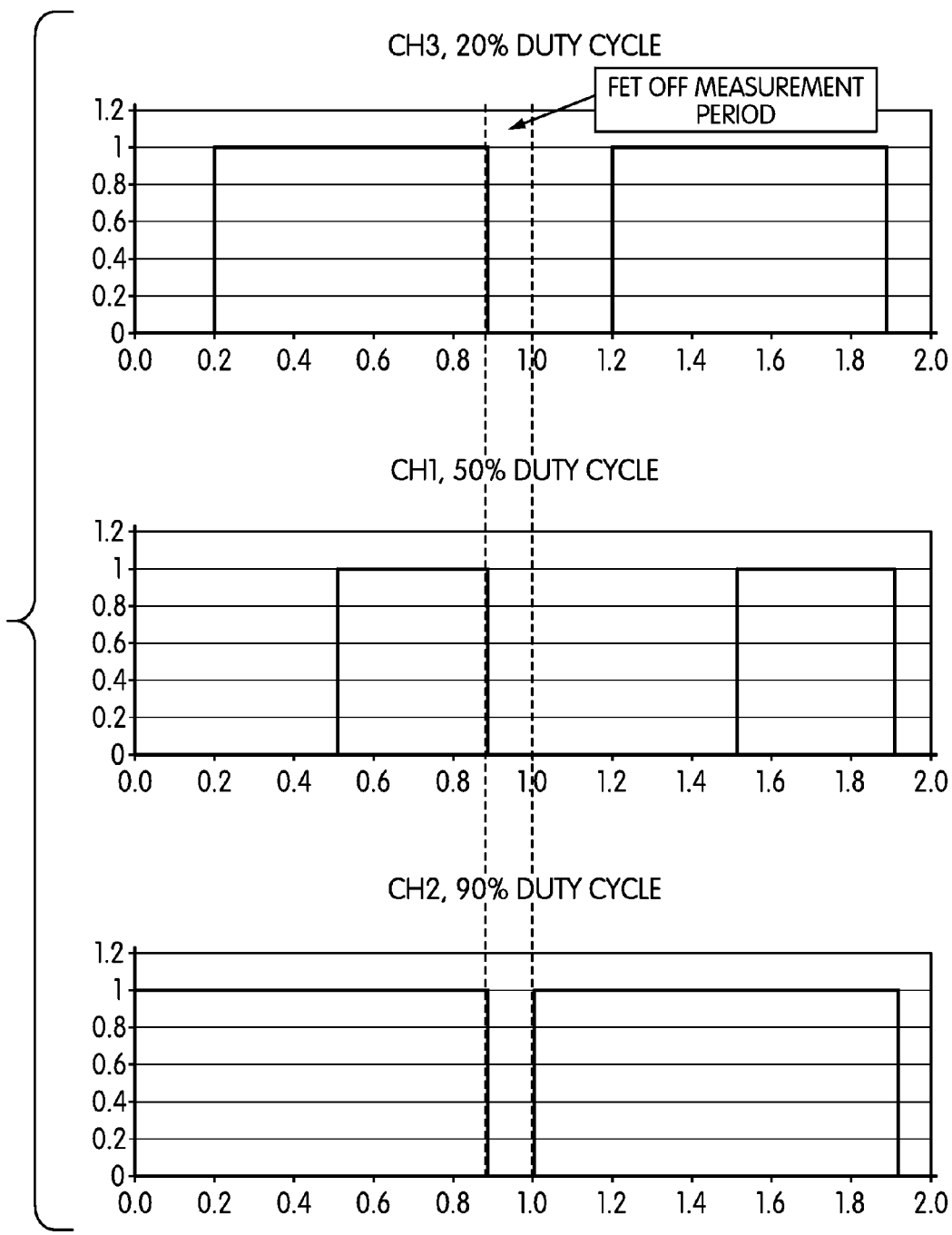
FIG. 13 depicts three different duty cycle profiles, wherein each duty cycle ends at about the same time so there is a period during which power is off for all heaters of a multiplexed system.

Because the microfluidic device 200 can have more than one microfluidic channel, channel cross talk can be an issue during OFF measurements. That is, if the power to one heater is off while power to an adjacent heater is on, there may be thermal and electrical cross talk between the heater(s) with power on and the heater(s) with power off, thereby affecting the temperatures derived for the power-off heaters. Each channel still needs individual control to maintain an even temperature distribution among the PCR area. The potential for crosstalk can be minimized by configuring the control system to make sure all channels are in the same state during the OFF measurements, as shown in FIG. 13. For example, according to one embodiment, all of the channels can be at a fixed PWM repetition rate, with only the duty cycle of the control signal being different for each channel to control the power to each channel. A maximum duty cycle (e.g., 90 percent) can be set and all channels can be measured in the FET OFF state in the remaining time (e.g., 10 percent). Similarly, a minimum duty cycle of 10% could be used to measure all channels in the FET ON state.

According to one embodiment of the present invention, the controller 550 can use a PID feedback equation to change the power output to the heaters 212a, 212b to meet the power requirements for the PCR profile. In order to use PID feedback, the system can first be calibrated by setting the output to a fixed power level and measuring the temperature. This can be done at several temperatures to develop an equation for voltage to temperature conversion. Alternatively, the Callendar-Van Dusen equation, as set forth below, may be used:

$$R_T = R(0°\text{ C.})(1 + AT + BT^2) \qquad \text{Equation 3}$$

where B is zero for the operating range to the microfluidic device 200. The equation thus can be solved for temperature as follows:

$$T = \frac{R_T - R_0}{AR_0} \qquad \text{Equation 4}$$

Where A is found by the following equation:

$$A = \frac{R(100°\text{ C.}) - R(0°\text{ C.})}{100 R(0°\text{ C.})} \qquad \text{Equation 5}$$

Typically, for platinum wires, $A \approx 0.004$.

Once the system is calibrated, the temperature can be measured by the controller 550 and the PID feedback equation can be used to change the power to meet the desired PCR profile. The PID feedback equation is given by:

$$\text{Output} = K_p \text{Error} + K_i \int \text{Error}(dt) + K_d d(\text{Error})/dt \qquad \text{Equation 6}$$

The coefficients Kp, Ki, and Kd can be determined by a temperature step response.

According to some embodiments, the heater controller 550 is a first order system with no time delay, so $K_d = 0$. $Kp = 1/(Ba*\tau)$ where $\tau$ is the time it takes a heater 212a or 212b to cool from a hot temperature to a cool temperature and Ba is the system gain. According to some embodiments, the hot temperature is 95° C. and the cool temperature is 54° C. Preferably, $\tau$ is about 0.4 and the system gain is about 2.5. Ki can be set to the $\tau$ to provide moderate control speeds with little overshoot. For more aggressive speeds, Ki can be set to some fraction of $\tau$ such as $\tau/5$, though doing so may result in the system having over/undershoot. According to an alternative embodiment of the present invention, $\tau$ can be the time a heater 212a or 212b takes to heat up from a cool temperature (e.g. 54° C.) to a hot temperature (95° C.).

Figure 14:
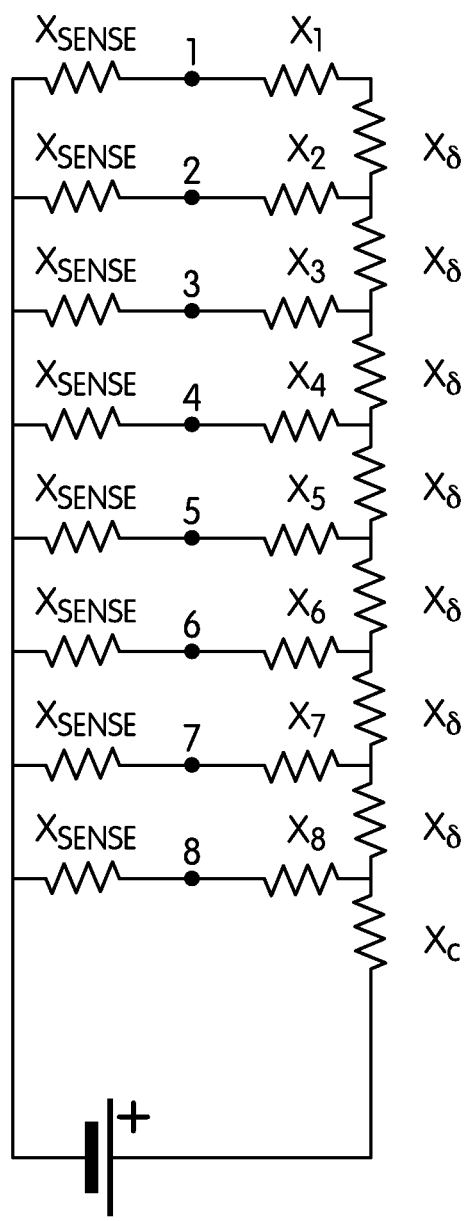
FIG. 14 depicts a resistive network of a microfluidic device with multiplexed resistive heaters, wherein the heater electrodes are used for both heating and temperature measurement.

As stated above, the heater signals can be multiplexed in different ways. Multiplexing a plurality of heater control signals results in a resistance network such as that shown in FIG. 14, for example. FIG. 14 represents the resistance network of an 8-channel microfluidic device according to one embodiment. In addition to the resistance of the plurality of thin-film heaters 212a and 212b (in this example: x1, x2, ..., x8), there exists a number of parasitic resistances such as, for example, xc for the common leads 316a or 316b and xδ for each of the spaces in 316a and 316b that separate thin-film heaters 212a and 212b. With only independent measurements made at points 1-8, the system may be underdetermined due to the common lead 316a or 316b and other parasitic resistances. Specifically, even with only 8 measurements the parasitic resistances may result in measurement errors due to system and environmental factors. A further aspect of the present invention utilizes a novel electrical measurement and drive circuit that can determine the temperature of such multiplexed resistive heaters.

According to embodiments of the present invention, PCR thermocycling is achieved by using resistive traces (such as, for example, platinum thin films) as thin film heaters 212a, 212b. Thin film heaters can also act as resistance temperature detectors (RTDs). As described above, to achieve fast response and increased measurement sensitivity, each heating element can be switched into separate "drive" or "measurement" states through the use of a switch (such as a transistor, relay, etc.). The "drive" state uses a lower resistance sense resistor in the voltage division circuit to maximize the current through the resistive heater and achieve fast heating rates. The "drive" state may or may not be used in conjunction with pulse width modulation (PWM). The "drive" state is also referred to as the "power on" state. The "measurement" state uses a moderate sense resistance to maximize measurement sensitivity (while minimizing self heating). The "measurement" state is also referred to as the "power-off" state.

In one embodiment of the present invention, two more switches per resistive heater are added as well as a common power supply switch that in combination allow for greater measurement flexibility and efficacy. Additionally, "open" and "supply" states are added to each channel. Furthermore, the common power supply may be included in the "open" or "closed" configuration. These modifications allow the power supply to be moved from the common lead to any lead desired. This allows the common lead parasitic resistance to be removed from the measurement in certain configurations.

Further, by making additional measurements the parasitic resistances can be explicitly determined, which removes a potential measurement error.

Figure 15:
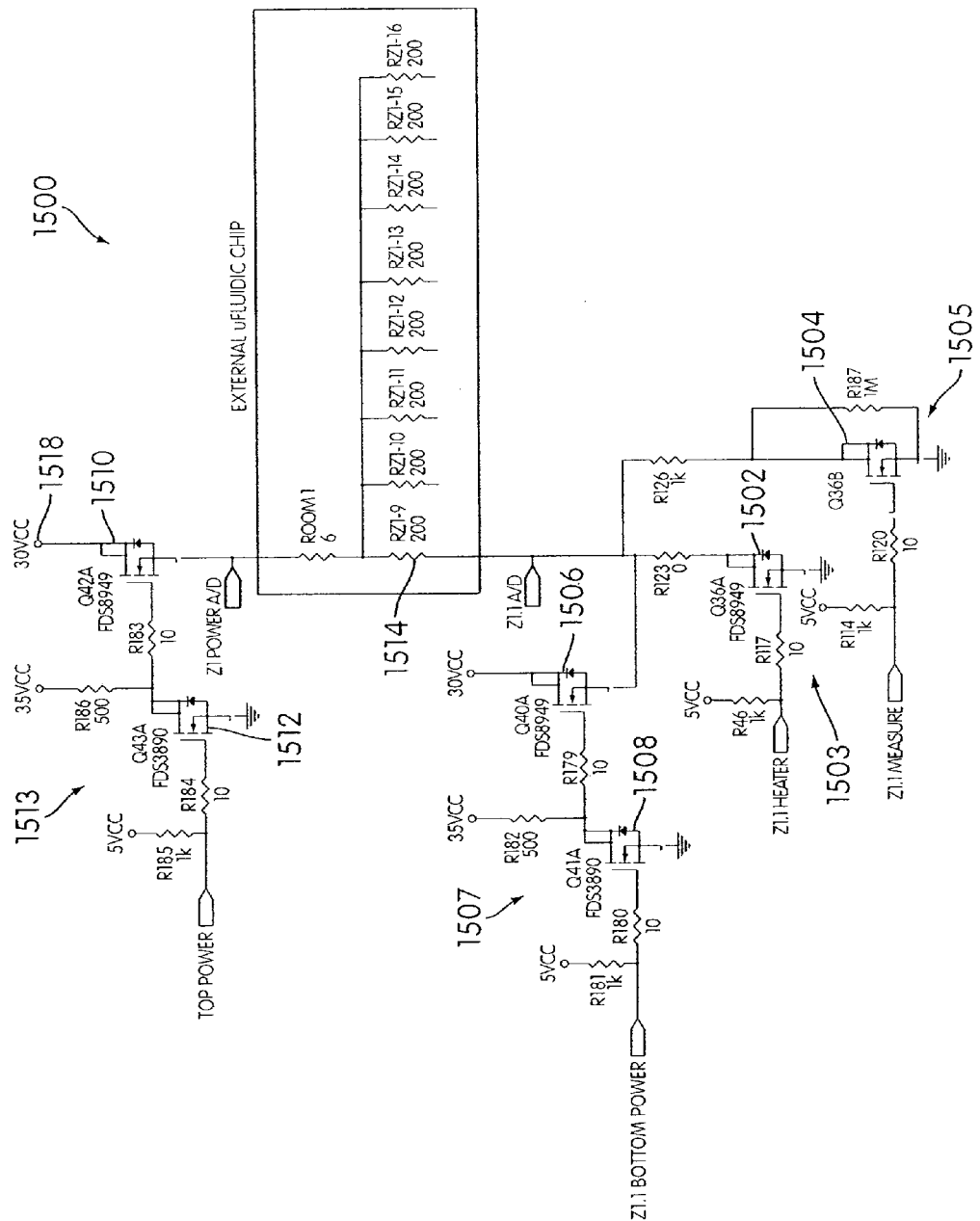
FIG. 15 depicts a diagram of a circuit configured to selectively disconnect a common lead from a power supply, selectively connect any of the resistive heaters channels to the power supply, or selectively remove any of the heater channels from the multiplex circuit.
Figure 16:
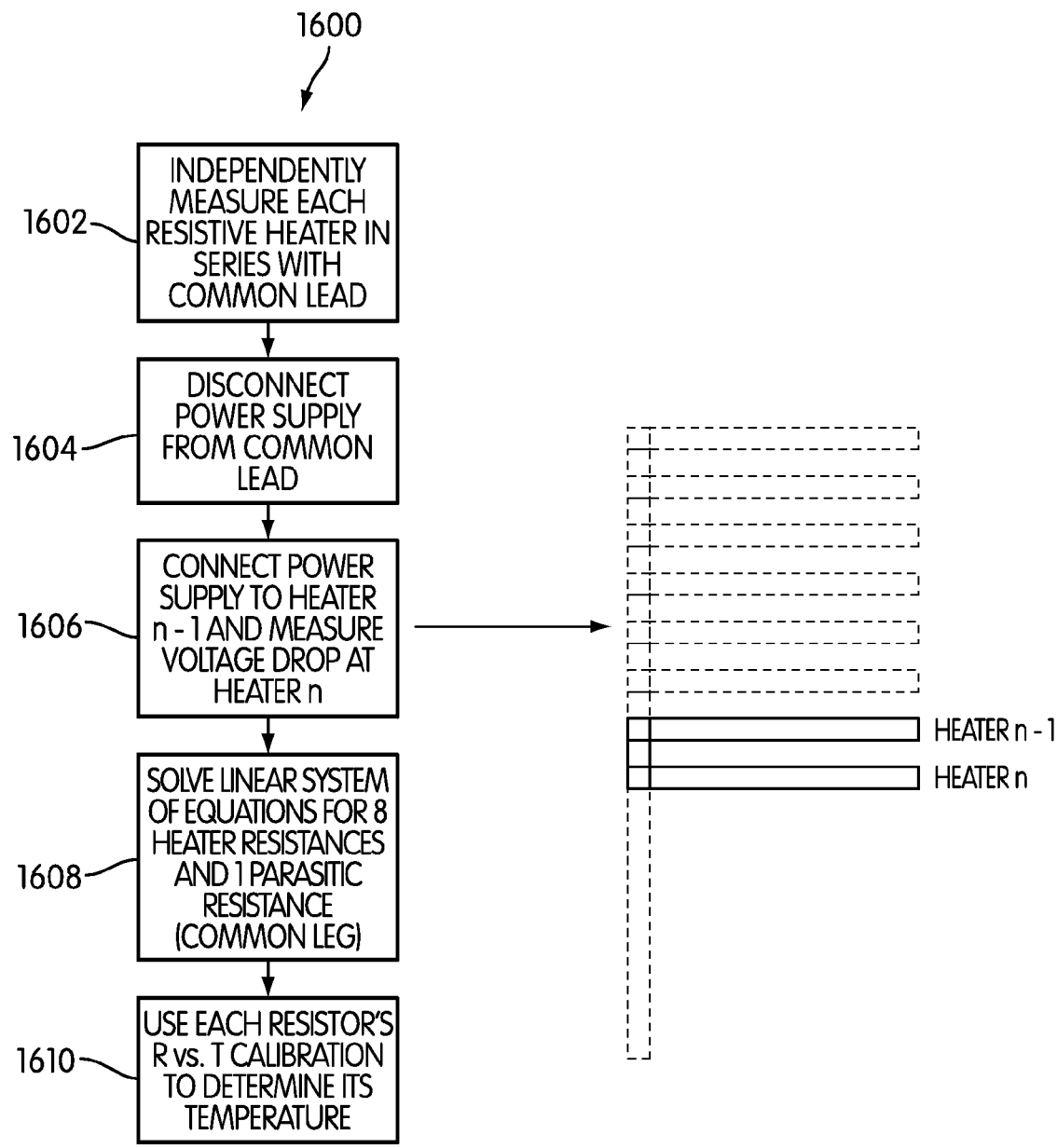
FIG. 16 depicts a flow chart showing a representative embodiment of a method for determining the temperatures of a plurality of multiplexed heaters.

A representative drive circuit 1500 capable of making these measurements is illustrated in FIG. 15. In this embodiment, switching is accomplished with electric switches (1502, 1504, 1506, 1508, 1510, 1512), which can be Metal Oxide Semiconductor Field Effect Transistors (MOSFET) switches that are driven by digital output lines on a high speed data acquisition system. FETs 1508 and 1512 have specifically been included as level shifting devices to increase the voltage at the gate of the primary switching FETs 1506 and 1510, respectively, which results in lower ON resistance switching and higher quality measurements. FIG. 15 shows the circuit for only one of the eight resistive heaters (e.g., resistive heater 1514) and the common lead.

Circuit branch 1513 may comprise electric switch 1512 and 1510 and may be used to connect or disconnect the common lead to or from power source 1518. Circuit branch 1507 includes electric switches 1506 and 1508 and can connect or disconnect resistive heater 1514 to or from the drive circuit branch 1503. Drive circuit branch 1503 is similar to the circuit shown in FIG. 12. Measurement circuit branch 1505 includes electric switch 1504 and shunt resistor R187, which acts as a shunt around switch 1504 when switch 1504 is OFF. With the transistor 1504 ON, the resistance measurements can be taken as normal. When transistor 1504 is OFF, however, then resistance measurements can still be taken due to the small current that still flows through large resistor R187.

Each of the remaining heater channels RZ1-10 to RZ2-16 also includes circuit branch 1507, drive circuit branch 1503 and measurement circuit branch 1505. With drive circuit 1500, the common lead can be disconnected from the power sources, each heater channel can be selectively connected to the power source, and each heater channel can be selectively removed from the resistive network. Drive circuit 1500 thus allows for isolated, power-on and power-off measurements.

With a plurality of channels the measurement combination possibilities are immense. In one embodiment, measurements can be made for the series resistance of any two resistors (common lead included), where the number of combinations is given by:

$$C = \frac{(n+1)!}{2 \cdot (n-1)!}$$ Equation 7 where n is the number of thin film heaters 212 (common lead excluded). The actual number of measurements required can be determined by persons of ordinary skill given their need for accuracy and the limitations of the data logging system.

Considering a resistive network with 8 heating elements (as shown in FIG. 14), resistance measurements of a subset of all of the possible measurements can be represented with a measurement matrix, such as A, which is shown below. The columns of A denote resistances, and the rows denote individual measurements. The product of A with the resistance vector x is equal to the measurements made during thermal control, vector b.

$$Ax = b$$ Equation 8

$$x = inv(A)b$$ Equation 9

Where:

$$A = \begin{bmatrix} 1 & 0 & 0 & 0 & 0 & 0 & 0 & 0 & 1 & 7 \\ 0 & 1 & 0 & 0 & 0 & 0 & 0 & 0 & 1 & 6 \\ 0 & 0 & 1 & 0 & 0 & 0 & 0 & 0 & 1 & 5 \\ 0 & 0 & 0 & 1 & 0 & 0 & 0 & 0 & 1 & 4 \\ 0 & 0 & 0 & 0 & 1 & 0 & 0 & 0 & 1 & 3 \\ 0 & 0 & 0 & 0 & 0 & 1 & 0 & 0 & 1 & 2 \\ 0 & 0 & 0 & 0 & 0 & 0 & 1 & 0 & 1 & 1 \\ 0 & 0 & 0 & 0 & 0 & 0 & 0 & 1 & 1 & 0 \\ 1 & 1 & 0 & 0 & 0 & 0 & 0 & 0 & 0 & 1 \\ 0 & 1 & 1 & 0 & 0 & 0 & 0 & 0 & 0 & 1 \\ 0 & 0 & 1 & 1 & 0 & 0 & 0 & 0 & 0 & 1 \\ 0 & 0 & 0 & 1 & 1 & 0 & 0 & 0 & 0 & 1 \\ 0 & 0 & 0 & 0 & 1 & 1 & 0 & 0 & 0 & 1 \\ 0 & 0 & 0 & 0 & 0 & 1 & 1 & 0 & 0 & 1 \\ 0 & 0 & 0 & 0 & 0 & 0 & 1 & 1 & 0 & 1 \end{bmatrix}$$

$x = [\, x_1 \;\; x_2 \;\; x_3 \;\; x_4 \;\; x_5 \;\; x_6 \;\; x_7 \;\; x_8 \;\; x_c \;\; x_\delta \,]'$ $b$ = vector of measurements recorded through data acquisition The individual resistances x can be determined through matrix inversion. However, the great flexibility of the measurement circuit and this algorithm allows for more measurements than unknowns, resulting in an overdetermined system. This overdetermined system can then be solved for an optimal solution that reduces the effect of random measurement errors. In one typical embodiment, the linear least squares technique is used to determine the optimal solution yielding estimates for all heater resistances along with the parasitic resistances xc and xδ. Finally, each resistor's resistance versus temperature calibration curve (typically of the form $R(T) = R(T_0)(1 + \alpha \Delta T)$) is used to determine its temperature, where $R(T)$=resistance at temperature T, $R(T_0)$=resistance at temperature $T_0$ and $\alpha$=the temperature coefficient of resistivity of the particular material.

The subset of resistance measurements may be taken according to a variety of different methods. FIGS. 16-21 illustrate several of the methods for taking resistance measurements in accordance with various embodiments. In method 1600 illustrated in FIG. 16, each resistance of each heater 212a or 212b can be measured in series with the common lead 316a or 316b, at step 1602. Next, at step 1604, the power supply $V_{cc}$ is disconnected from the common lead. The power supply is then connected to heater n−1, and the voltage drop is measured at heater n at step 1606. Next, at step 1608 a system of linear equations for 8 heater resistances and 1 parasitic resistance can be solved. Each resister's R vs. T calibration data is used to determine the temperature of the resistor at step 1610.

Figure 17:
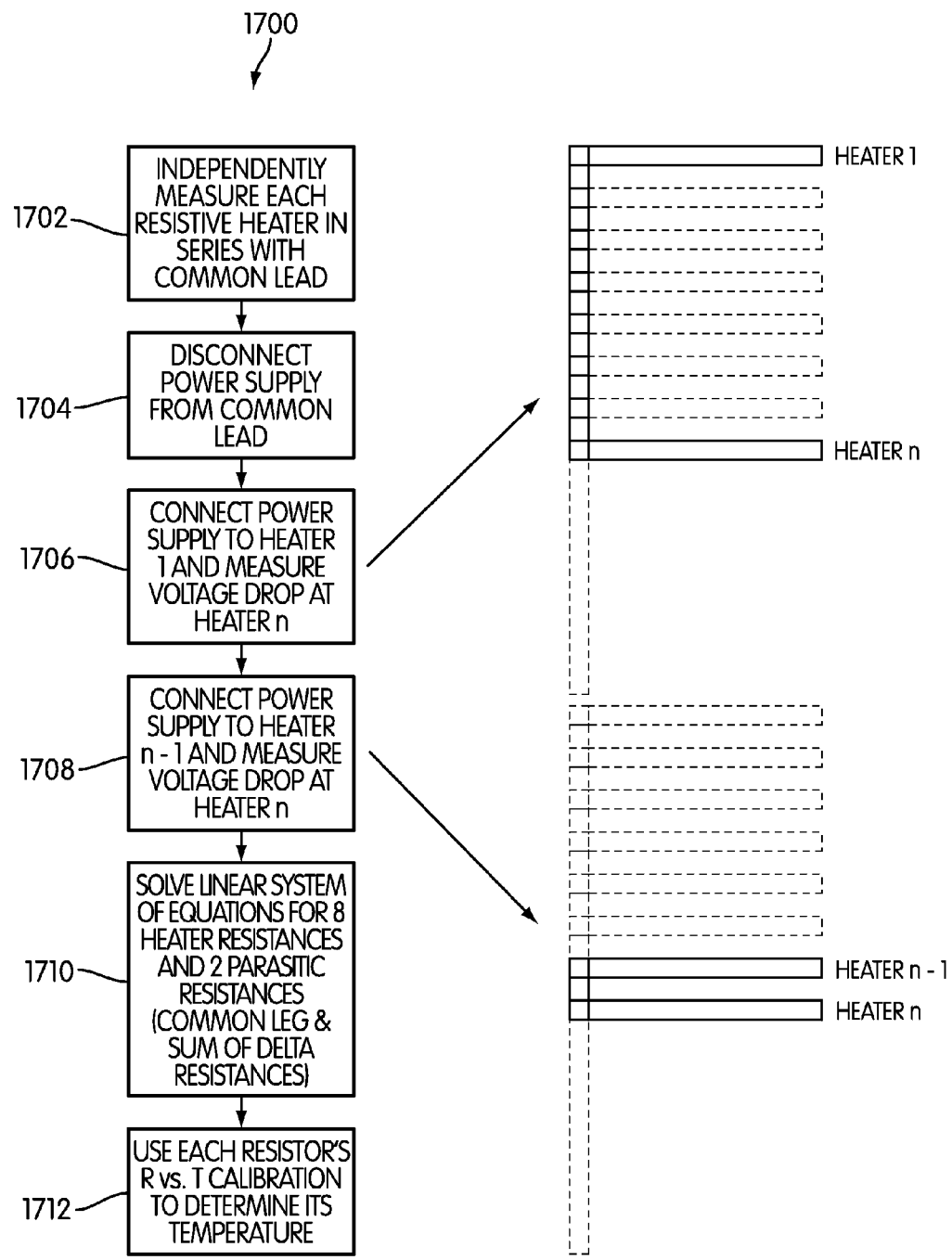
FIG. 17 depicts a flow chart showing a first alternative embodiment for determining the temperatures of a plurality of multiplexed heaters.

FIG. 17 illustrates a method 1700 in which, at step 1702, each of the heaters 212a or 212b is measured in series with the common lead 316a or 316b. The power supply is then disconnected from the common lead at step 1704. Next, at step 1706, the power supply is connected to heater 1 and the voltage drop is measured at the $n^{th}$ heater. At step 1708, the power supply is then connected to the $(n-1)^{th}$ heater and the voltage drop at heater n is measured. Next, at step 1710, a system of linear equations for 8 heater resistances and 2 parasitic resistances can be solved. At step 1712, each resistor's R vs. T calibration can then be used to determine the temperature.

Figure 18:
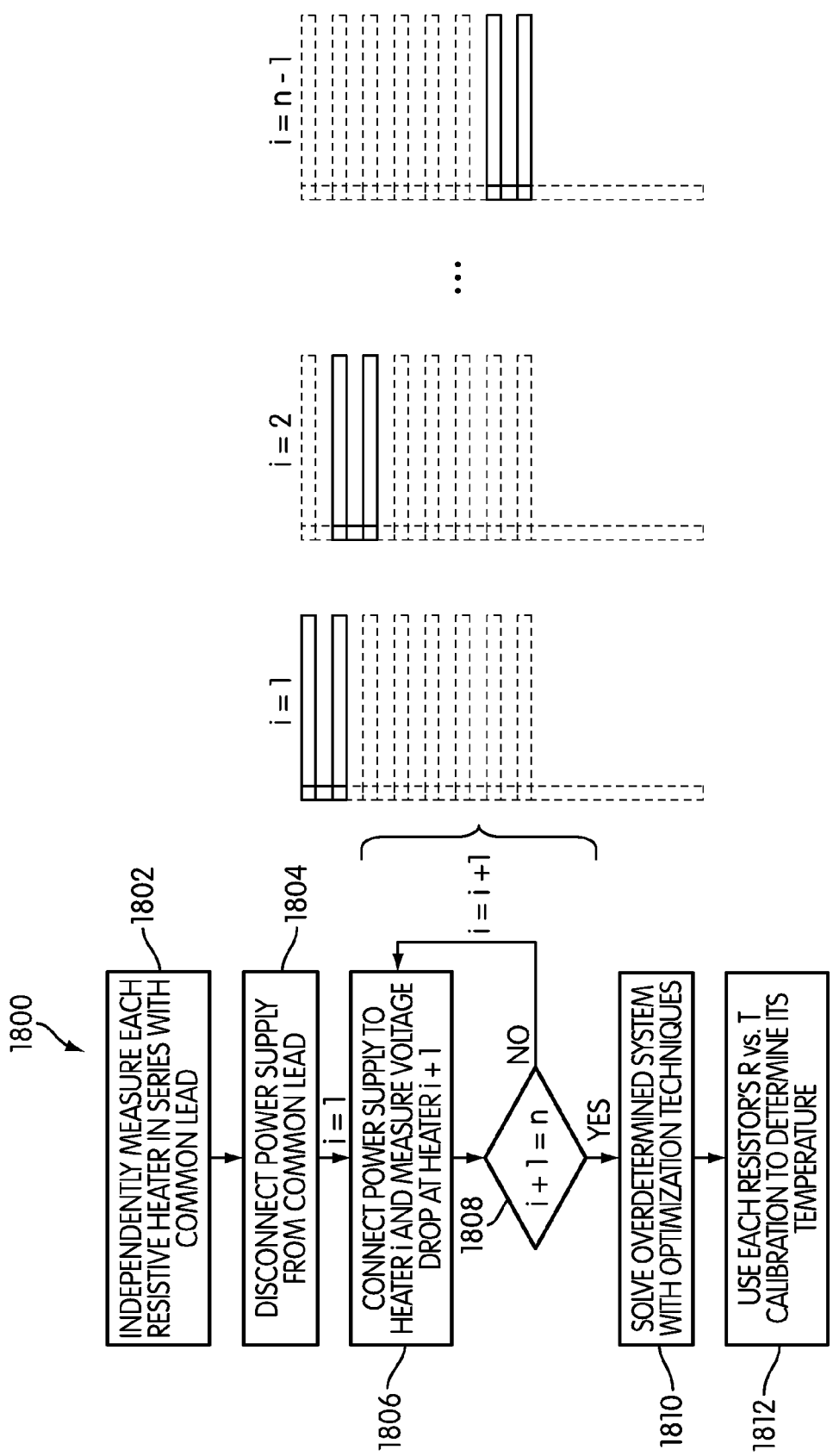
FIG. 18 depicts a flow chart showing a second alternative embodiment for determining the temperatures of a plurality of multiplexed heaters.

FIG. 18 illustrated method 1800 in which, at step 1802, each heater is measured in series with the common lead. At step 1804, the power supply is then disconnected from the common lead and a counter variable i is set to 1. At step 1806, the power supply is then connected to heater i and the voltage is measured at heater i+1. At step 1808, it is determined whether i+1=n. If not, then the counter is incremented and the next measurements are taken at step 1806. If i+1 is equal to n, then the over determined system can be solved with optimization techniques at step 1810. Finally, at step 1812, each resistor's R vs. T calibration is used to determine its temperature.

Figure 19:
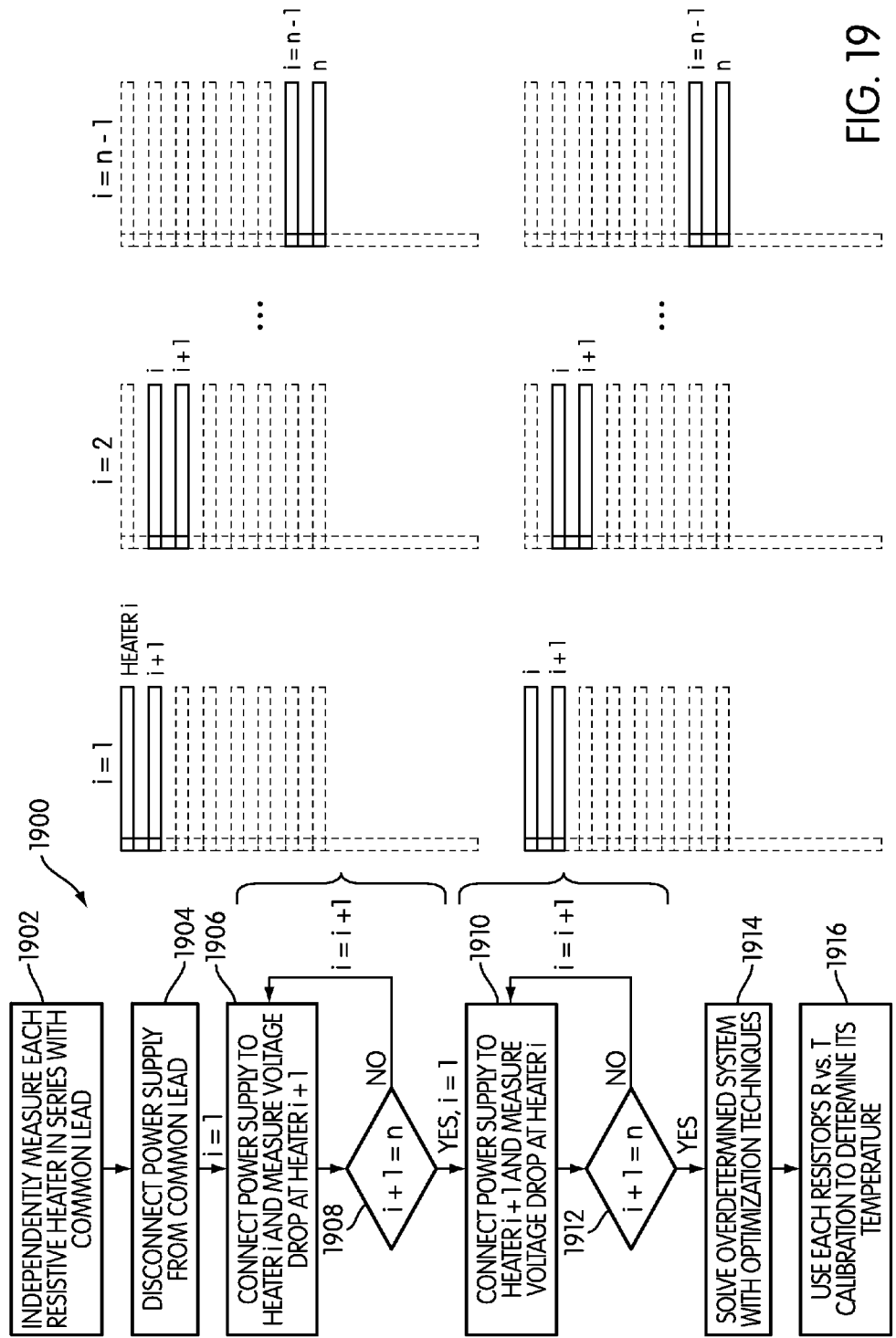
FIG. 19 depicts a flow chart showing a third alternative embodiment for determining the temperatures of a plurality of multiplexed heaters.

FIG. 19 illustrates method 1900 which is similar to method 1800 but includes additional steps. As in the method illustrated in FIG. 18, each heater is measured in series with the common lead at step 1902. The power supply is then disconnected from the common lead at step 1904, and i is set to equal 1. Next, at step 1906, the power supply is connected to heater i, and the voltage drop at heater i+1 is measured. This is repeated until i+1=n, as shown at step 1908. If not, then i is incremented and step 1906 is repeated. If i+1 does equal n, then i is reset to one and the power supply is connected to heater i+1 and the voltage drop at heater i is measured at step 1910. This is repeated for i=1 to n. At step 1912, it is determined whether i+1=n. If not, i is incremented by 1 and the process returns to step 1910. Otherwise, the process continues to step 1914. At step 1914, the overdetermined system can be solved with optimization techniques. Finally, at step 1916, each resistor's R vs. T calibration can be used to determine its temperature.

Figure 20:
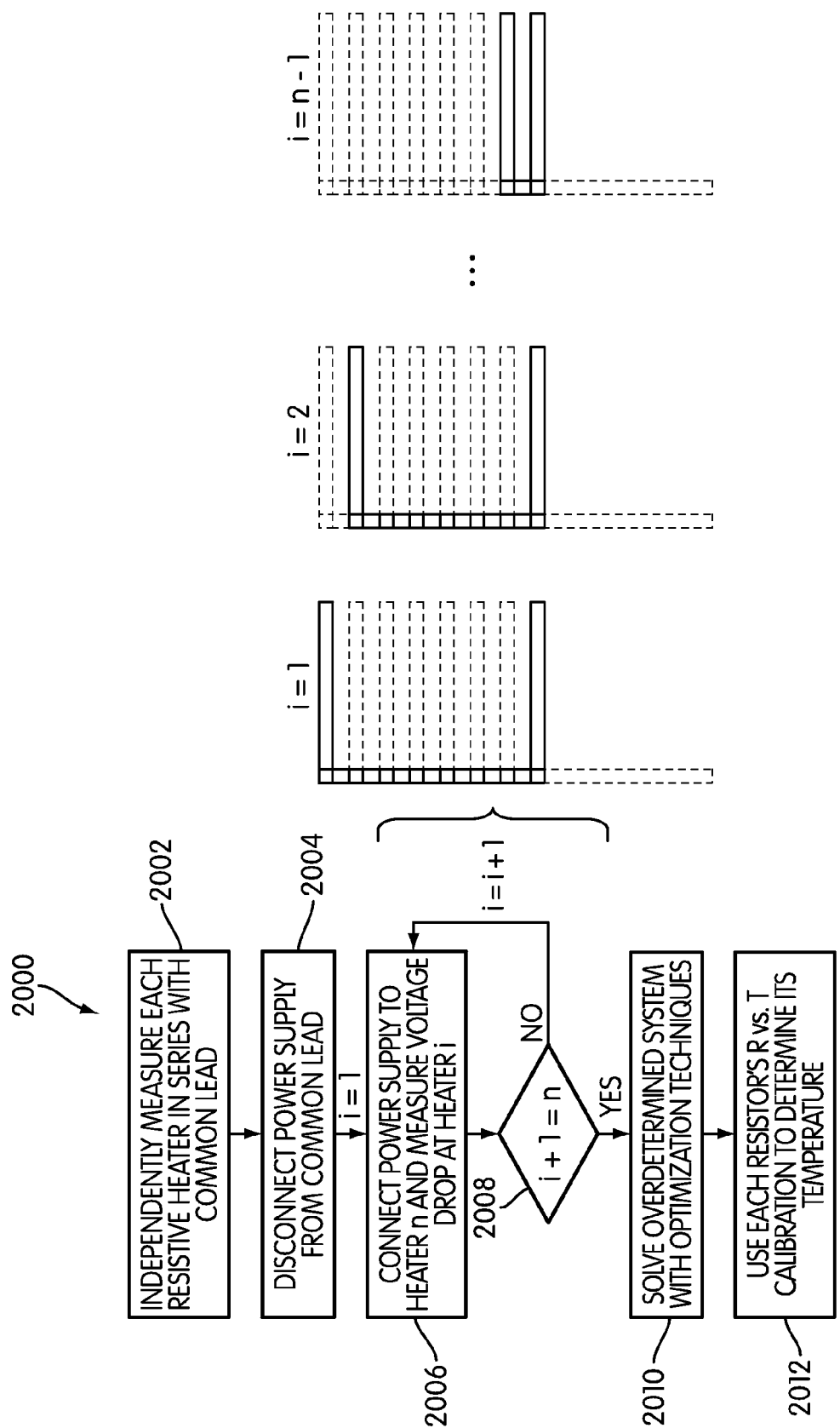
FIG. 20 depicts a flow chart showing a fourth alternative embodiment for determining the temperatures of a plurality of multiplexed heaters.

FIG. 20 illustrates method 2000 which can be characterized in that it keeps the power supply connected to the same heater such as, for example, heater n. First, each heater is measured in series with the common lead at step 2002. Next, at step 2004, the power supply is disconnected from the common lead, and i is set to 1. Next, the power supply is connected to heater n, and the voltage drop is measured across heaters 1 through n−1 at steps 2006 and 2008. The over-determined system can then be solved with optimization techniques, as shown in step 2010. Finally, each resistor's R vs. T calibration can be used to determine its temperature at step 2012.

Figure 21:
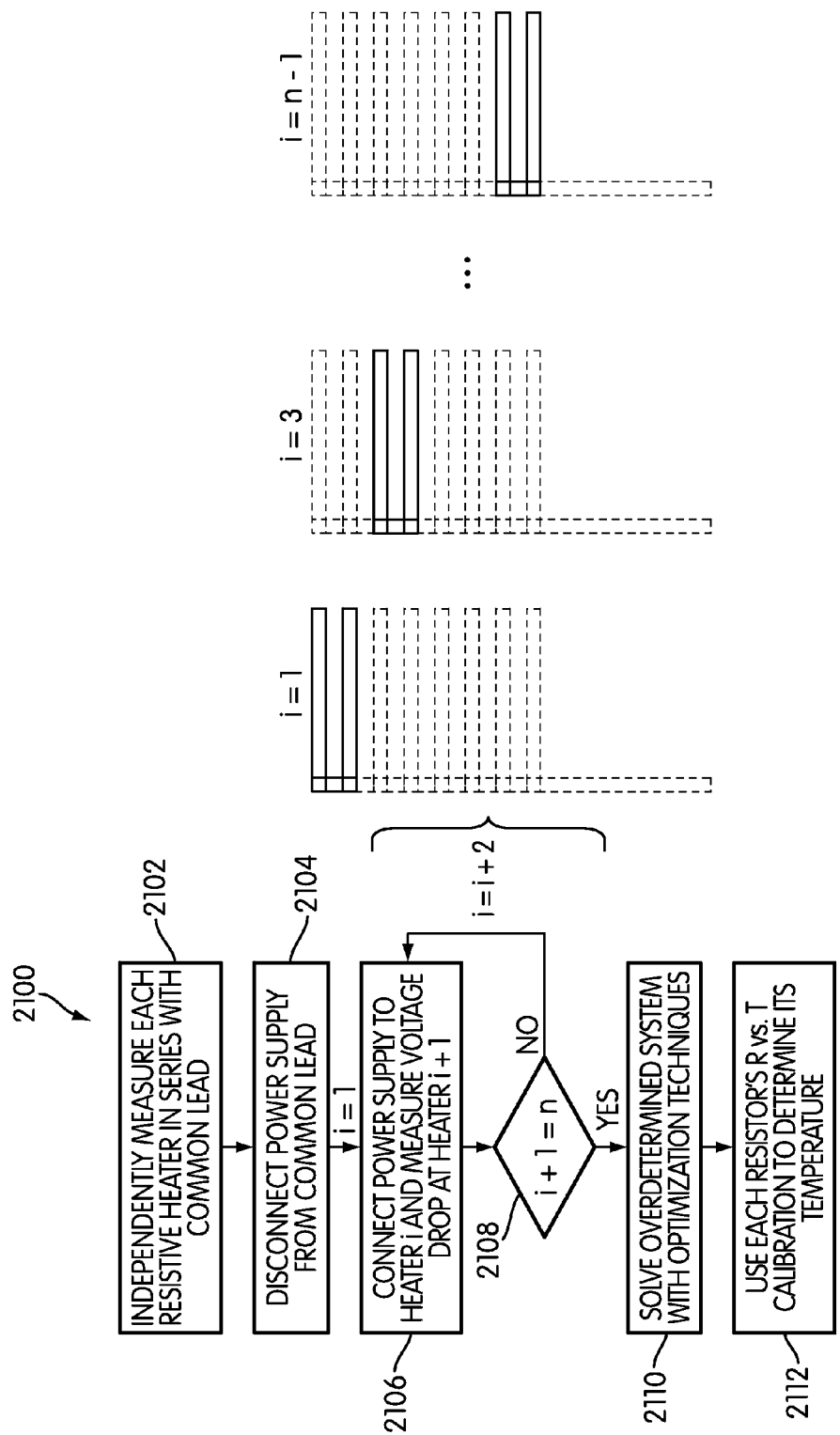
FIG. 21 depicts a flow chart showing a fifth alternative embodiment for determining the temperatures of a plurality of multiplexed heaters.

FIG. 21 illustrates method 2100 in which, at step 2102, each heater is measured in series with the common lead. The power supply is then disconnected from the common lead and a counter variable i is set to 1 at step 2104. The power supply is then connected to heater i and the voltage is measured at heater i+1 at step 2106. At step 2108, it is determined whether i+1=n. If not, then the counter is incremented by two and the next measurements are taken at step 2106. If i+1 is equal to n, then the over determined system can be solved with optimization techniques at step 2110. Finally, at step 2112, each resistor's R vs. T calibration is used to determine its temperature.

Figure 22:
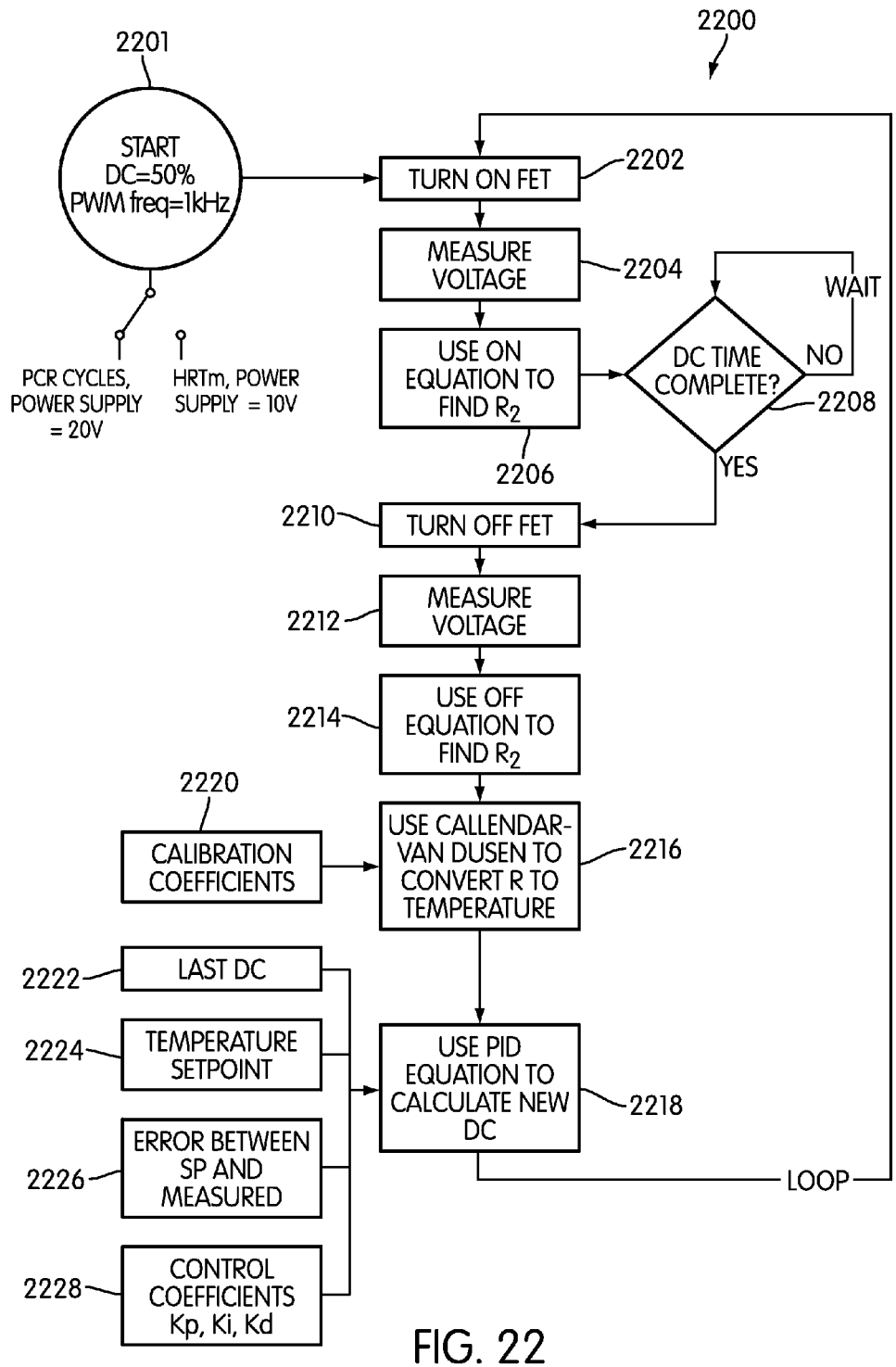
FIG. 22 depicts a flow chart showing a method for PWM closed-loop control of a resistive heater.

In one embodiment, illustrated in FIG. 22, PWM and PID are used for both PCR and thermal melt. In this case, different supply voltages, duty cycles, and PID control parameters (the proportional, integral, and derivative terms) can be implemented for the two different processes. For example, a larger supply voltage (e.g. 20 Volts) may be desired for PCR to effect faster response time, while a more modest voltage may be desired for high resolution thermal melt (HRTm) (e.g. 10 Volts) to ensure accurate temperature measurement. The duty cycles required would be determined by the closed loop PID control system and could range from 0 to 100%. For example, for the transition from denaturation to annealing (e.g. 95° C. to 55° C.), the duty cycle might initially be reduced to 0% to achieve rapid cooling. The duty cycle would then be increased as the heater temperature approaches the set point, with the exact values determined using PID. Similarly, for the transition from the annealing to extension phases (e.g. 55° C. to 72° C.), the duty cycle might initially be set to 100% to heat quickly. The duty cycle would then be reduced as the set point is approached.

FIG. 22 illustrates a method 2200 of PWM closed loop control of the heaters 212a or 212b according to an embodiment of the present invention. The method could be used to control the heaters in either the PCR zone 204 (PCR Cycles, Power Supply=20V) or the thermal melt zone 206 (high resolution thermal melt, Power Supply=10V). At step 2201, the duty cycle is set to some initial value (e.g., 50%) and the PWM frequency is also set to an initial value (e.g., 1 kHz). The FET or FETs can then be turned ON at step 2202 and the voltage across the heaters 212a or 212b measured at step 2204. The ON equation (equation 1, above), can then be used to calculate R2 (see FIG. 12). Next, at 2208, a determination is made as to whether the FET has been ON long enough for the specified duty cycle. If yes, at steps 2210-2214, the FET is turned off, the voltage drop across the heater 212a or 212b can be measured, and the OFF equation (equation 2, above) can be used to determine the value of R2. At step 2216, the Callendar-Van Dusen equation can be used to convert R into temperature factoring in the calibration coefficients 2220, which may be downloaded from a storage device. Next, at step 2218, a new duty cycle can be calculated using a PID equation factoring in the last duty cycle 2222, the temperature set point 2224, the error between the set point and the measured temperature 2226, and the control coefficients Kp, Ki, and Kd 2228. Finally, the FET is turned back on for the new duty cycle as control loops back to step 2202.

Figure 23:
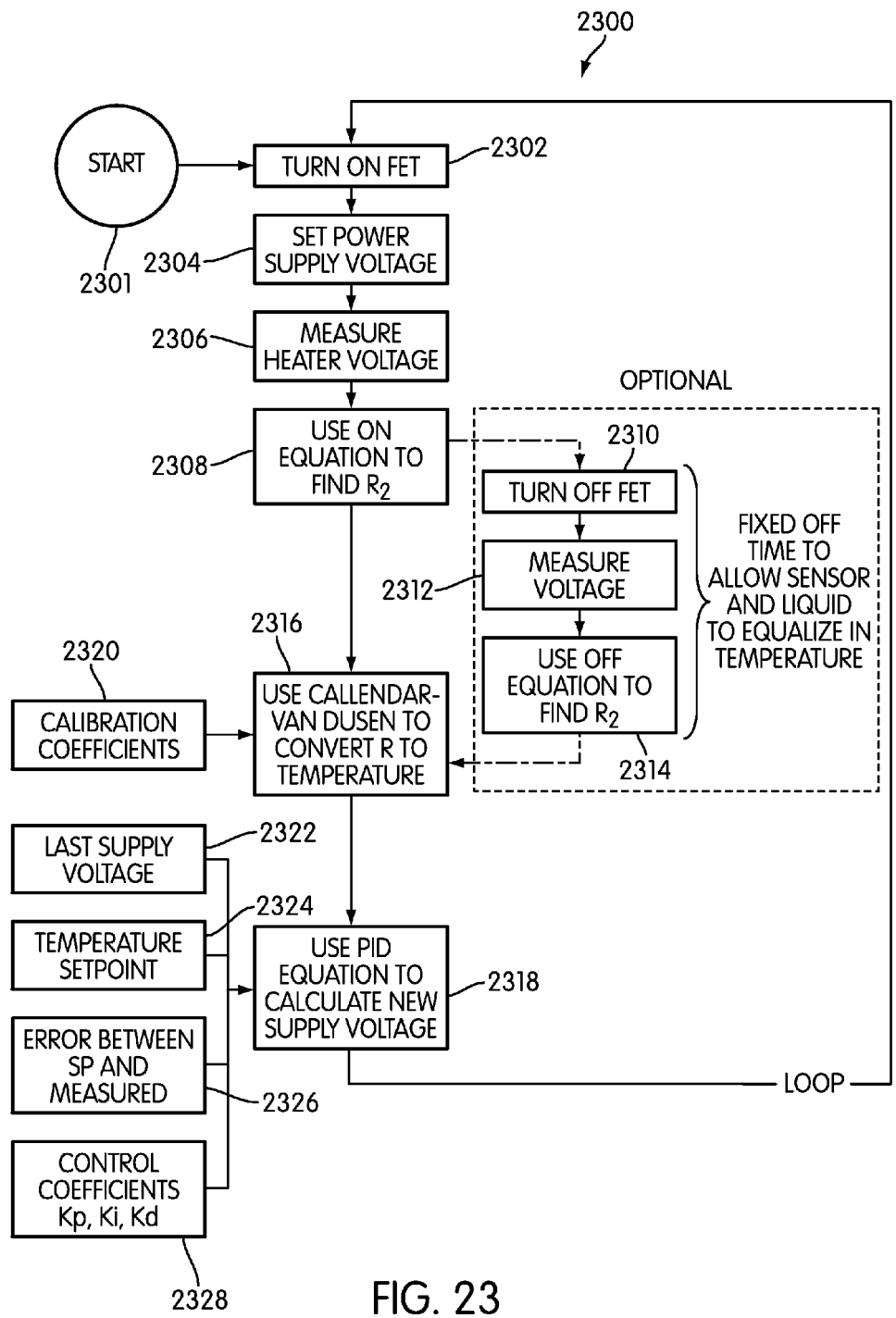
FIG. 23 depicts a flow chart showing a method for analog closed-loop control of a resistive heater.

Alternatively, in another embodiment, closed loop control could be used, but PWM drive could be replaced with analog drive in which heating is controlled by varying the voltage rather than the duty cycle. For example, FIG. 23 illustrates method 2300 which is an analog closed loop control used to obtain the desired temperature. In accordance with this embodiment, after start at step 2301, the FET is turned on at step 2302. The power supply voltage is then set to an initial level at 2304. The voltage drop across the heater is measured at step 2306 and the ON equation (equation 1, above) is used to find R2 value at step 2308. Next, at step 2316, the Callendar-Van Dusen equation is used to convert the resistance value into temperature factoring in the calibration coefficients 2320. Next, at step 2318, a PID equation is used to calculate a new supply voltage factoring in the last supply voltage 2322, the temperature set point 2324, the error between the temperature set point and the measured temperature 2326, and control coefficients 2328. The new supply voltage is set as control loops back to step 2302.

According to an alternative embodiment, after step 2308, the FET is turned OFF for a fixed amount of time to allow the sensor and the liquid in the microfluidic channel to equalize in temperature at step 2310. The voltage drop across the heater is measured at step 2312, and the OFF equation (equation 2, above) is used to calculate R2 at step 2314.

Figure 24:
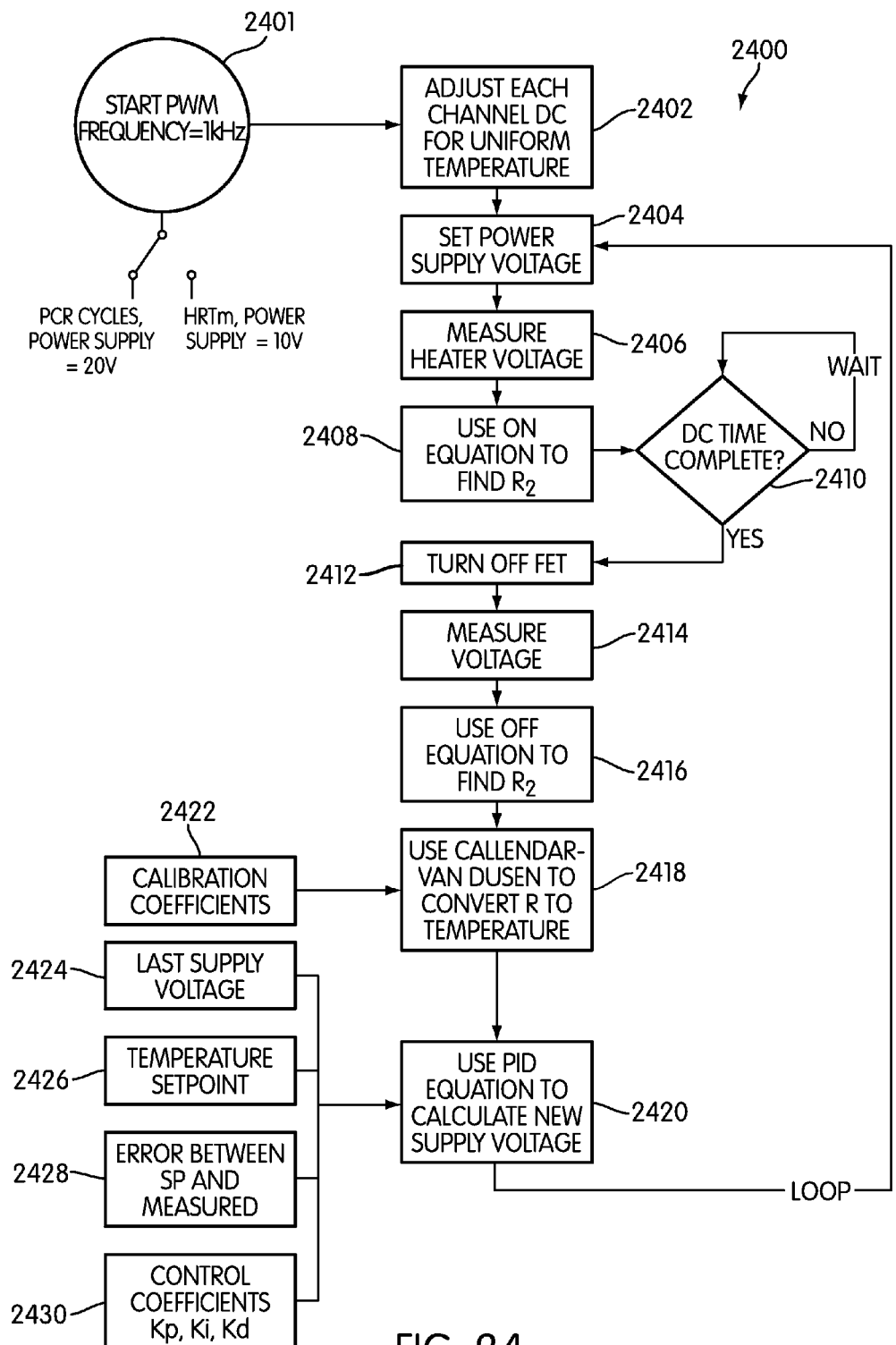
FIG. 24 depicts a flow chart showing a method for PWM closed-loop control for heating different resistive heaters differently to account for manufacturing variations or temperature gradients.

In another embodiment, closed loop control is utilized which involves using PWM to heat different resistive heaters differently to account for manufacturing variations or temperature gradients. As illustrated in FIG. 24, different duty cycles could be used for each heater to ensure temperature uniformity. According to method 2400, the PWM frequency is set to a predetermined frequency (e.g., 1 kHz) at step 2401. Each channel's duty cycle is adjusted for uniform temperature at 2402. Next, at step 2404, the supply voltage is set to an initial value. The voltage drop across the heater is then measured at step 2406, and the ON equation is used to calculate the value of R2 at step 2408. The FET is kept on until the duty cycle time is complete, as determined at step 2410. Next, at step 2412, the FET is turned OFF and the voltage drop across the heater is measured at step 2414. Next, the OFF equation can be used in step 2416 to find R2. The Callendar-Van Dusen equation can then be used to convert the resistance value measured for R2 into a temperature value at step 2418 factoring in calibration coefficients 2422.

Finally, a PID equation is used to calculate a new supply voltage at step 2420 factoring in the last supply voltage 2424, the temperature setpoint 2426, the error between the temperature setpoint and the measured temperature 2428, and the control coefficients (Kp, Ki, and Kd). The new supply voltage is set as the control loops back to step 2404.

Figure 25:
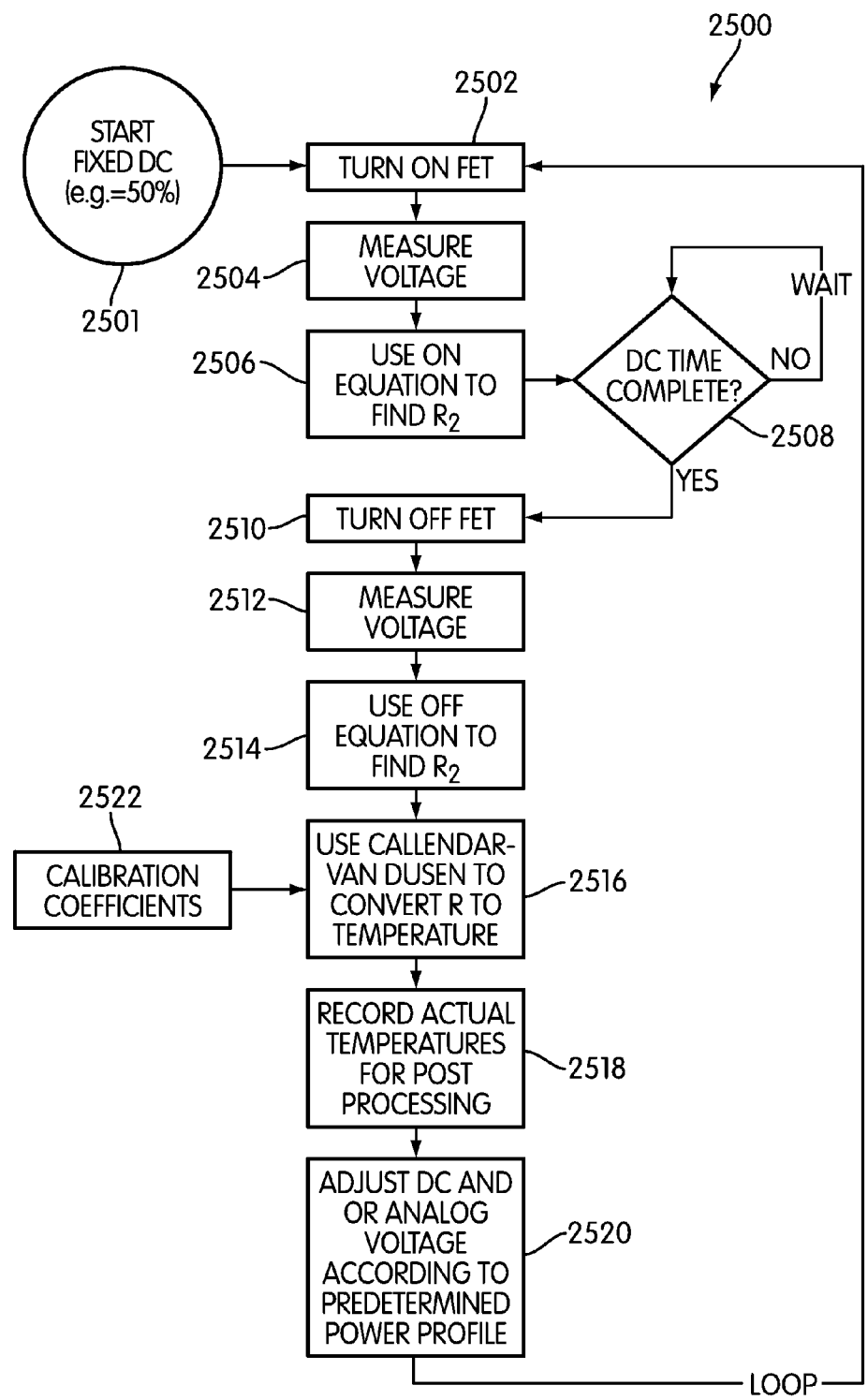
FIG. 25 depicts a flow chart showing a method for open-loop control of a resistive heater electrode.

In another embodiment, closed loop control could be used for the PCR process (as described above), and thermal melt could be performed in an open loop configuration. As illustrated in FIG. 25, a method of open loop thermal melting would involve increasing the supply voltage through a controllable power supply while monitoring the temperature of the heaters using the measurement control circuit. Another method of open loop thermal melting would involve ramping the duty cycles (e.g. from 30% to 80%) while monitoring the temperature of the heaters 212a, 212b.

In another embodiment, PCR could be performed in open loop configuration while thermal melt is performed using PID. For PCR, different drive currents and/or duty cycles would be used to achieve different temperatures. The different drive currents (which are predetermined) may be achieved by a programmable power supply or through the use of a digital potentiometer (Rdp), which controls the total resistance and thus the drive current. The PCR drive voltage could be always on (100% duty cycle, i.e. traditional direct current (DC)) or PWM could be used with fixed but predetermined duty cycles less than 100%. In this configuration, PWM could also be used to heat different resistive heaters 212a, 212b differently to account for manufacturing variations or temperature gradients.

According to another embodiment of the present invention, open loop control can be performed by the method 2500 illustrated in FIG. 25. In this embodiment, the control signal is given an initial duty cycle (e.g., 50%) at step 2501. Next, at step 2502, the FET is turned ON and the voltage drop across the heater is measured at step 2504. The ON equation can then be used to determine the value of R2 at step 2506. The FET is held in the ON state until the appropriate amount of time for the duty cycle has passed, as determined at step 2508. Next, at step 2510, the FET is turned to the OFF state and the voltage drop across the heater is measured at step 2512. The OFF equation can then be used to determine the value of R2 at step 2514. Callendar-Van Dusen equations can then be used to convert R2's resistance value into a temperature value in step 2516 using the heater's calibration coefficients 2522. Next, the actual temperatures can be recorded in step 2518, and the duty cycle and/or the analog voltage can be adjusted according to a predetermined power profile in step 2520. The FET is then turned ON again as control loops back to step 2502.

Embodiments of the present invention have been fully described above with reference to the drawing figures. Although the invention has been described based upon these preferred embodiments, it would be apparent to those of skill in the art that certain modifications, variations, and alternative constructions could be made to the described embodiments within the spirit and scope of the invention.

What is claimed is:

1. In a microfluidic device incorporating thin-film heaters within a plurality of microfluidic channels to effect a biological reaction with multiple steps each requiring a different temperature, a method of controlling the microfluidic with pulse width modulation (PWM) comprising:
   generating a set of calibration data while calibrating a modulation frequency with a temperature by measuring a cooling rate of the thin-film heaters between pulses and adjusting the modulation frequency based upon the measured rate;
   using the calibration data to generate a PWM control signal for the thin-film heaters designed to bring the heaters to a desired temperature for a first step in the biological process;
   adjusting the PWM signal to achieve a temperature for an appropriate time required by said first step; and
   adjusting the PWM signal to achieve a desired temperature for a second step in the biological process.

2. The method of claim 1, wherein the PWM signals are differentially sequenced to minimize current draw and power spiking on the system power supply.

3. The method of claim 2, wherein differentially sequencing the PWM signals comprises a multiplexed sequence among 3 or more microfluidic channels.

4. The method of claim 1, wherein the biological reaction is a polymerase chain reaction.

5. The method of claim 4, wherein the polymerase chain reaction occurs within a first temperature zone.

6. The method of claim 1, wherein the biological reaction is a high resolution thermal melt.

7. The method of claim 6, wherein the high resolution thermal melt occurs within a second temperature zone.

8. The method of claim 1, wherein a thin-film heater is associated with each microfluidic channel.

9. The method of claim 1, wherein a common electrical contact is associated with all of the microfluidic channels.

10. The method of claim 1, wherein the step of generating calibration data comprises:
   (a) applying electrical power to all heater electrodes;
   (b) measuring a voltage drop across each of the heater electrodes to determine individual electrode resistance values;
   (c) computing a nominal heater power based on the individual heater electrode resistance values;
   (d) applying the nominal heater power to the heater electrodes for a pre-determined calibration pulse time;
   (e) collecting heater electrode resistance measurements for a predetermined collection time at a predetermined sampling rate;
   (f) using the measurements to compute a thermal decay time constant reflecting the rate at which the heater electrode cools when the power is off; and
   (g) computing an optimal pulse width modulation frequency based on the decay time information.

11. The method of claim 1, wherein the biological reaction is a polymerase chain reaction in a first temperature zone and a high resolution thermal melt in a second temperature zone.

12. A method of controlling a microfluidic device comprising a plurality of thin-film heaters that heat a plurality of parallel microfluidic channels to effect a biological reaction, said method comprising:
   providing control circuitry configured to generate PWM control signals to drive the thin-film heaters, wherein each channel is in thermal communication with at least one of the plurality of thin-film heaters;
   differentially sequencing the pulse width modulation control signals to said thin-film heaters, wherein the PWM control signals associated with different channels are phase shifted relative to each other so as to minimize current draw and power spiking on a system supplying power to said microfluidic device.

13. The method of claim 12, wherein the pulse with modulation control signals are differentially sequenced among 3 or more microfluidic channels.

14. The method of claim 12, wherein the pulse with modulation control signals are differentially sequenced among two banks of parallel microfluidic channels.

15. The method of claim 12, wherein the biological reaction is a polymerase chain reaction.

16. The method of claim 12, wherein the biological reaction is a thermal melt.

17. The method of claim 12, wherein a thin-film heater is associated with each microfluidic channel.

18. The method of claim 12, wherein a common electrical contact is associated with all of the microfluidic channels.

* * * * *